US012690971B2

(12) United States Patent (10) Patent No.: US 12,690,971 B2
Cullum et al. (45) Date of Patent: Jul. 28, 2026

(54) REVISION-IMPLANT RECEIVER, AN IMPLANT ANCHOR AND METHOD OF USE THEREOF

(71) Applicant: MATORTHO LIMITED, Surrey (GB)

(72) Inventors: Charles Jonas Ambrose Cullum, Surrey (GB); Simon Nicholas Collins, Surrey (GB)

(73) Assignee: MATORTHO LIMITED, Surrey (GB)

( * ) Notice: Subject to any disclaimer, the term of this patent is extended or adjusted under 35 U.S.C. 154(b) by 767 days.

(21) Appl. No.: 18/003,430

(22) PCT Filed: Jun. 30, 2021

(86) PCT No.: PCT/GB2021/051667
§ 371 (c)(1),
(2) Date: Dec. 27, 2022

(87) PCT Pub. No.: WO2022/003356
PCT Pub. Date: Jan. 6, 2022

(65) Prior Publication Data
US 2023/0233328 A1      Jul. 27, 2023

(30) Foreign Application Priority Data
Jul. 1, 2020      (GB) ..................................... 2010084

(51) Int. Cl.
A61F 2/30                (2006.01)

(52) U.S. Cl.
CPC ...... A61F 2/30 (2013.01); *A61F 2002/30205* (2013.01)

(58) Field of Classification Search
CPC .. A61F 2/30; A61F 2/3662; A61F 2/38; A61F 2/389; A61F 2/30734
See application file for complete search history.

(56) References Cited

U.S. PATENT DOCUMENTS

| | | | |
|---|---|---|---|
| 4,094,017 A | 6/1978 | Matthews et al. | |
| 4,262,368 A | 4/1981 | Lacey | |
| 4,878,919 A | 11/1989 | Pavlansky | |
| 5,314,481 A | 5/1994 | Bianco | |
| 8,753,399 B2* | 6/2014 | Sharifi-Mehr | A61F 2/4425 623/17.13 |
| 9,629,727 B2* | 4/2017 | Baynham | A61F 2/4611 |

(Continued)

FOREIGN PATENT DOCUMENTS

| | | |
|---|---|---|
| DE | 3822854 A1 | 1/1990 |
| DE | 19509037 C1 | 9/1996 |

(Continued)

OTHER PUBLICATIONS

European Examination cited in EP 21746087.2, dated Jan. 14, 2025, 7 pages.

(Continued)

*Primary Examiner* — Brian A Dukert
(74) *Attorney, Agent, or Firm* — LEASON ELLIS LLP

(57) ABSTRACT
A revision-implant receiver (18) is provided for supporting an implant (20) of a revision joint replacement (10). The revision-implant receiver (18) comprises a first receiver element (22) and a second receiver element (24). The first receiver element (22) and the second receiver element (24) are engaged with each other via a hinge element (26).

11 Claims, 14 Drawing Sheets

(56) References Cited

U.S. PATENT DOCUMENTS

2009/0149963  A1    6/2009  Sekel
2019/0070008  A1    3/2019  Bauer et al.
2019/0110907  A1    4/2019  Yoko et al.

FOREIGN PATENT DOCUMENTS

DE          19735875  A1    3/1999
WO          2017070348  A1    4/2017

OTHER PUBLICATIONS

British Search Report cited in GB2406735.7, dated May 22, 2024, 3 pages.
British Examination Report in GB Application No. 2010084.8, mailed Mar. 26, 2024 (3 pages).
International Search Report for corresponding International Application No. PCT/GB2021/051667, dated Sep. 30, 2021.
Search Report for corresponding British application No. GB2010084. 8, dated Dec. 17, 2020.
International Preliminary Report on Patentability for corresponding International Application No. PCT/GB2021/051667, dated Dec. 13, 2022.

* cited by examiner

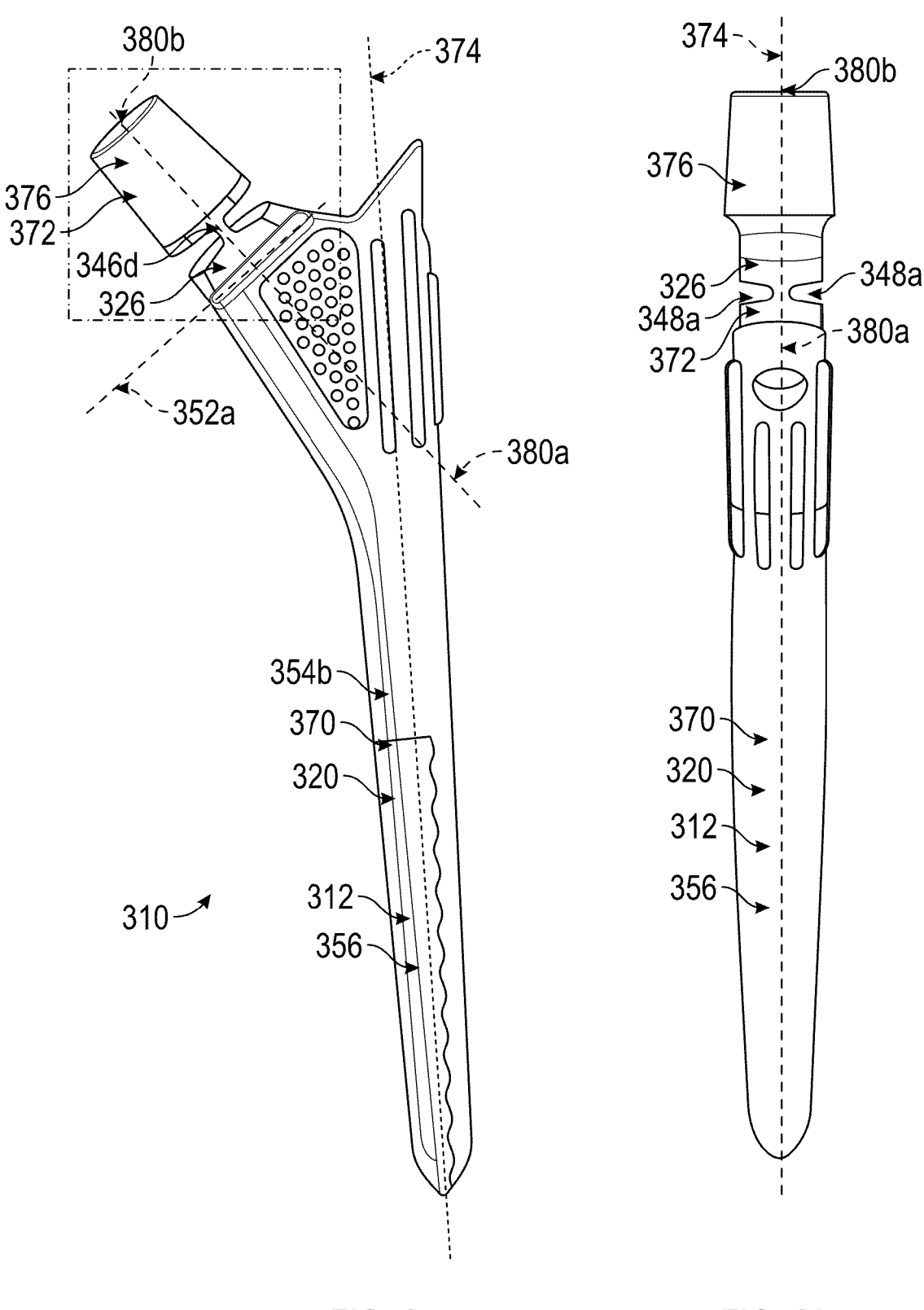
FIG. 15         FIG. 16

REVISION-IMPLANT RECEIVER, AN IMPLANT ANCHOR AND METHOD OF USE THEREOF

CROSS-REFERENCE TO RELATED PATENT APPLICATIONS

This application is a U.S. National Stage Application under 35 U.S.C. § 371 of International Patent Application No. PCT/GB2021/051667 filed Jun. 30, 2021, which claims the benefit of priority of British Patent Application No. GB2010084.8 filed Jul. 1, 2020, both of which are incorporated by reference in their entireties. The International Application was published on Jan. 6, 2022, as International Publication No. WO/2022/003356A1.

The present invention relates to a hinged receiver which is insertable into a bone during revision arthroplasty and which receives a revision implant. The present invention also relates to a kit including the hinged receiver and at least part of an implant for revision arthroplasty. The present invention also pertains to a method of use of the hinged receiver. The present invention also relates to a method of improving the angular orientation of an implant.

Arthroplasty is the replacement of a joint, such as a knee, with an artificial joint. When the whole natural knee is first replaced, this is called a primary total knee replacement or pTKR. However, a pTKR can fail for a number of reasons including loosening, poor function, wear, and infection, such that the pTKR needs to be replaced. A revision total knee replacement or rTKR is generally implanted to replace such a failed pTKR. This involves removing the entire pTKR and implanting a set of new rTKR components to the further diseased or compromised remaining bone. Both rTKR and pTKR aim to place the implants in a pre-determined position and orientation relative to the native anatomy in order to restore the knee's function as best as possible.

However, rTKR surgery is typically more complex than pTKR surgery due to the unknown state of the soft tissues and native bone stock following the impact of a multitude of potential failure mechanisms and the difficulty in removing the primary knee. A requirement for successful fixation of the rTKR components is finding and locating good quality bone, which tends to be further away from the bearing surface than that used for the primary implant.

In order to cater for the unknowns intraoperatively, rTKR systems tend to offer a variety of interchangeable and adjustable bearing and fixation options.

Distal and posterior augments may be inserted between the bone and the inner face or backside, non-bearing surfaces of an implant to provide anterior-posterior adjustment and/or proximal-distal adjustment in the sagittal plane of the joint, and to provide a bone void or space filling. Medial-lateral adjustment in the coronal plane of the joint is done via a stem offset and/or medial-lateral translation of a stem within an implantable cone or sleeve.

Furthermore, a fragile or damaged bone may not be able to accommodate the forces of the revision implant without any additional structural support. A solution is to insert a metaphyseal cone into the shallow metaphyseal bone. The interface between the metaphyseal cone and the implant is via cement. Alternatively, a metaphyseal sleeve having a short stem or no stem may be used. The sleeve provides deep metaphyseal fixation. However, a sleeve requires a mechanical interlock between the sleeve and the implant. Furthermore, metaphyseal cones and sleeves are monobloc and non-adjustable.

Thus, rTKRs are usually modular with an array of options for the diaphyseal stem (length, diameter, cemented or cementless, offset), augments (thickness, side, size, angle) and metaphyseal fixation (cone or sleeve, size, side), which can be used individually or in combination, as required. This modularity means that surgery is lengthy and complicated. Additionally, an extensive inventory needs to be stocked which is both expensive and space consuming.

The present invention seeks to provide a solution to these problems.

According to a first aspect of the present invention, there is provided a revision-implant receiver for supporting an implant of a revision joint replacement, the revision-implant receiver comprising a first receiver element and a second receiver element which is engaged via a hinge element with the first receiver element. The revision-implant receiver enables angular adjustment in at least one plane of an implant received therein. Furthermore, the adjustability may reduce the inventory that must be stocked.

Preferably, the first receiver element and the second receiver element define together a central cavity for receiving a stem of the implant therein, and the hinge element comprises a pair of bendable linking portions between the first receiver element and a second receiver element, each bendable linking portion of the pair being positioned on either side of the central cavity to define a hinge axis. Each linking portion being positioned around the cavity does not obstruct or substantially obstruct the cavity. As such, the linking portions do not prevent or inhibit the insertion of a stem of the implant into the cavity.

Optionally, each linking portion may comprise a waisted portion for enabling bending. Furthermore, the at least one linking portion may comprise at least one concave surface for providing the waisted portion. Each linking portion has a narrowest portion or minimum cross-sectional area, width, or thickness to enable controlled bending thereat.

Beneficially, the first receiver element and/or second receiver element may comprise a recessed portion and a said linking portion may extend from the recessed portion, the recessed portion thereby elongating the linking portion for distributing bending along the linking portion. The recessed portion may be provided in a spacer segment of the hinge element. Furthermore, the linking portion and the recessed portion may meet at a junction, the linking portion transitioning continuously into the recessed portion at the junction for preventing or inhibiting forces being concentrated at the junction. These features reduce or prevent the formation of a stress raiser.

Beneficially, an outer surface of the linking portion and/or the said recessed portion may be recessed radially inwardly relative to an outer surface of one or both the first receiver element and second receiver element, and/or wherein an inner surface of the linking portion and/or the said recessed portion may be recessed radially inwardly relative to an inner surface of one or both the first receiver element and second receiver element. The linking portion, by having a thinner lateral extent than the rims of the first receiver element and/or second receiver element, may be easier to bend. The linking portion may be recessed relative to either or both the inner surface and the outer surface of one or both the first receiver element and second receiver element.

Additionally, the first receiver element and/or the second receiver element may have a circular cross-section and the hinge axis may extend along a diameter of the first receiver element and/or the second receiver element. The linking portions are preferably diametrically opposed to each other on either side of the cavity. The hinge axis is centrally positioned. In other words, the range of the angular adjustment of the second receiver element is symmetrical about the first receiver element.

Beneficially, the hinge axis may extend in one of: an anterior-posterior direction for enabling angular adjustment of the second receiver element relative to the first receiver element in a coronal plane, and a medial-lateral direction for enabling angular adjustment of the second receiver element relative to the first receiver element in a sagittal plane. Optimising the angular orientation of the implant in the sagittal and/or coronal planes improves the fit and therefore the durability of the implant.

The term "coronal plane" used herein and throughout is defined as or intended to mean the plane which divides the relevant joint into posterior and anterior portions. The coronal plane (C) is illustrated in FIG. 1. Similarly, the term "sagittal plane" used herein and throughout is defined as or intended to mean the plane which divides the relevant joint into medial and lateral portions. The sagittal plane (S) is illustrated in FIG. 1. A third plane called the transverse plane (T) is also shown in FIG. 1. For clarity, an angle describing angular re-orientation in the coronal plane may be referred to as a "coronal angle" or a "varus/valgus angle". An angle describing an angular re-orientation in the sagittal plane may be referred to as a "sagittal angle" or a "flexion angle".

Preferably, the hinge element comprises a second pair of bendable linking portions between the first receiver element and the second receiver element, each bendable linking portion being positioned on either side of the central cavity and defining a second hinge axis. Furthermore, the second hinge axis may be non-parallel with the first said hinge axis. Two pairs of linking portions may provide redundancy or robustness against breakage. Two parallel, and preferably, spaced-apart, hinge axes may increase the angular range of re-orientation of the second receiver element relative to the first receiver element. Two non-parallel, and preferably spaced-apart, hinge axes enable re-orientation of the second receiver element relative to the first receiver element in two non-parallel planes.

Optionally, the second hinge axis may be perpendicular to the first said hinge axis. The two planes in which the implant may be adjusted are perpendicular to each other. In particular, if the first said hinge axis enables angular adjustment in one of the sagittal plane and the coronal plane of the joint, the perpendicular second hinge axis enables angular adjustment in the other of the sagittal plane and the coronal plane.

Additionally, the hinge element may comprise a spacer segment which may be positioned between the first receiver element and the second receiver element, said spacer segment being hingeably engaged with the first receiver element by the first said pair of bendable linking portions, and with the second receiver element by the second pair of bendable linking portions such that the second hinge axis is spaced-apart from the first said hinge axis. By being spaced-apart along a longitudinal axis of the revision-implant receiver, the first pair of linking portions does not prevent or inhibit bending about the second pair of linking portions, and vice-versa.

Preferably, the first said pair of bendable linking portions is integrally formed as a one piece with the spacer segment and the first receiver element; and/or the second pair of bendable linking portions is integrally formed as a one piece with the spacer segment and the second receiver element. The ease of manufacture is increased.

Optionally, the first receiver element or an inner surface thereof may be or be substantially a truncated cone. Furthermore, the second receiver element may be a trapezium in cross-section in the coronal plane, and one of: a circle, an ellipse, an oval, and a rectangle with one or more rounded edges and/or one or more rounded corners in in cross-section in a transverse plane. These geometries may further increase the angular range in at least one direction. The term "trapezium" used herein and throughout is defined as or intended to mean a four-sided geometric shape having at least one pair of parallel bases.

Optionally, the revision-implant receiver may be a femoral receiver or a tibial receiver. The revision-implant receiver may be adapted for use in the femur, whether to receive part of a knee implant or part of a hip implant. The revision-implant receiver may be adapted for or configured for use in the tibia, to receive part of a knee implant. Preferably, the revision-implant receiver is only adapted or adaptable for use in exactly one location due to anatomical and/or mechanical constraints. It could however be envisioned that the revision-implant receiver may be adapted or adaptable for use in more than one location, such that it may be used interchangeably in either end of the femur and/or in the tibia, by way of example only.

According to a second aspect of the present invention, there is provided an implant anchor for supporting a bearing surface of an implant, the implant anchor comprising a stem having a first stem portion and a second stem portion which is engaged via a hinge element with the first stem portion. The hinge element of the implant stem enables angular adjustment of the bearing surface. The hinged implant stem may be provided instead of a said hinged revision-implant receiver. In this case, less bone may need to be removed to accommodate the revision-implant receiver. Alternatively, the hinged implant stem may be provided in addition to the hinged revision-implant receiver. Having at least two and potentially three or more hinge elements may enable the angular adjustment to be more fine-tuned, particularly if the hinge elements enable re-orientation in different planes.

Advantageously, the hinge element may comprise at least one bendable linking portion defining a hinge axis. A hinge element having one linking portion is easier to manufacture, whilst a plurality of linking portions may provide redundancy or strength.

Beneficially, the stem may be or be substantially circular in cross-section along at least a majority of its longitudinal extent, although a minority of the longitudinal extent may be envisioned. Furthermore, the or each bendable linking portion may extend along at least a major extent of a characteristic or major length, which is preferably here a diameter, of the stem, although along a minor extent of the characteristic length may be envisioned instead. Although the stem is circular in cross-section, non-circular may be envisioned, such as oval, ellipse, curved and/or non-curved stem cross-sections may be envisioned. The range of angular adjustment of the implant bearing is symmetrical about the stem. In other words, the pivot of the hinge is centrally positioned.

Additionally, the hinge element may further comprise a spacer segment, and a second bendable linking portion having a second hinge axis, the first said bendable linking portion and the second bendable linking portion being spaced-apart by the spacer segment, and the first said hinge axis and the second hinge axis being non-parallel with each other for enabling angular adjustment in two distinct planes. Additional hinges enable more fine-tuning of the orientation of the bearing surface.

Furthermore, the implant anchor and/or the stem thereof may be connectable to the bearing surface by comprising a first connector portion and the bearing surface comprising a second connector portion, the first and second connector portions being complementarily engageable with each other. Optionally, the implant anchor and/or stem may be connectable to the bearing surface by being at least one of: engageable by interference fit, boltable, screwable, connectable via an adhesive, and cementable to the bearing surface. The implant bearing is separably connectable with the stem and/or implant anchor. This allows modularity or interchangeability of bearings, which can be used to improve the fit of the implant. Alternatively, the implant anchor and the bearing surface may be integrally formed.

According to a third aspect of the present invention, there is provided an implant-replacement anchoring kit, comprising a revision-implant receiver, preferably in accordance with the first aspect of the invention, and an implant anchor, preferably in accordance with the second aspect of the invention. Optionally, the anchoring kit may additionally comprise the bearing surface of the implant. The kit, comprising the hinged receiver and at least the hinged stem, provides additional degrees of freedom to adjust the position and orientation of the implant whilst reducing the inventory that needs to be stocked. If the stem and the implant bearing are non-integrally formed, a range of intraoperatively interchangeable implant bearings may be used to provide the best fit.

According to a fourth aspect of the present invention, there is provided an implant comprising an implant anchor, preferably in accordance with the second aspect of the invention, and a bearing surface, wherein the implant anchor is connected to the bearing surface by being integrally formed therewith. The ease of manufacture may be increased, reducing costs. The ease of assembly may be also be increased such that surgery time is reduced.

According to a fifth aspect of the present invention, there is provided an implant anchor for supporting a bearing surface of an implant, the implant anchor comprising a first portion and a second portion which is hingeably engaged with the first portion. The angular orientation of the implant is adjustable.

According to a sixth aspect of the present invention, there is provided a method of improving the angular orientation of an implant in revision arthroplasty, the method having the steps of: a] providing a revision-implant receiver, preferably in accordance with the first aspect of the invention, and a revision implant; and b] re-orienting the second receiver element about the hinge element relative to the first receiver element and inserting a stem of the revision implant into the re-oriented revision-implant receiver. The position and angular orientation of the revision implant are adjustable.

According to a seventh aspect of the present invention, there is provided a method of improving the angular orientation of an implant in revision arthroplasty, the method having the steps of: a] providing a revision implant and a revision-implant receiver, either or each of the revision implant and the revision-implant receiver having two hingeably connected portions; and b] adjusting the relative angle between the two hingeably connected portions of one or both the revision implant and the revision-implant receiver to improve the angular orientation of the revision implant in one or more planes, which may be the coronal plane and/or the sagittal plane. Angular adjustment in at least one plane of a relevant joint, preferably the coronal plane and/or the sagittal plane, is enabled.

The invention will now be more particularly described, by way of example only, with reference to the accompanying drawings, in which:

FIG. 15 shows a side view of an embodiment of an implant anchor of a femoral component of a revision hip replacement, in accordance with the second aspect of the invention;

FIG. 16 shows a back view of the implant anchor of FIG. 15;

Figure 1:
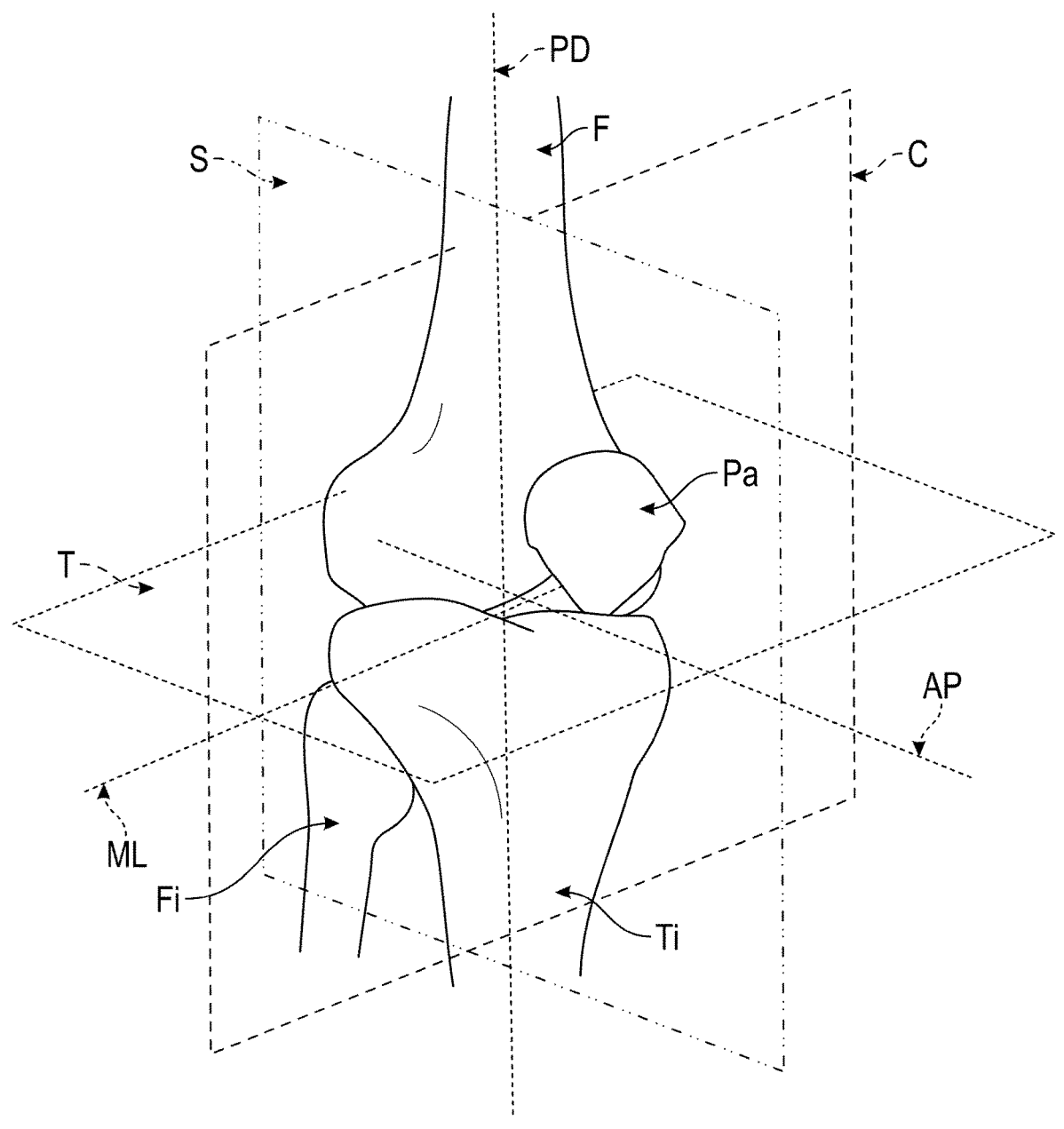
FIG. 1 shows a perspective representation of a knee, indicating the above-mentioned sagittal plane, the above-mentioned coronal plane, and a transverse plane thereof, with skin, muscles and ligaments omitted for clarity.

Referring firstly to FIG. 1, there is shown a typical human knee, and more specifically the bone structure thereof, with the ligaments, the skin and the muscles omitted for clarity. In particular, there is shown the femur F, the tibia Ti, the fibula Fi and the patella Pa. FIG. 1 also illustrates the coronal plane C, indicated as dashed lines; the sagittal plane S, indicated as dash-dot-dot lines and the transverse plane T, indicated in dotted lines. FIG. 1 also indicates in dotted lines the proximal-distal axis PD, the medial-lateral axis ML, and the anterior-posterior axis AP. The transverse plane T is the plane normal to the proximal-distal axis PD.

The portion of the femur F adjacent to the tibia Ti is conventionally referred to as the "distal" femur whilst the portion of the femur F which is remote relative to the tibia Ti and/or adjacent to the acetabulum, not shown, is referred to as the "proximal" femur. The portion of the tibia Ti which is adjacent to the femur F is conventionally referred to as the "proximal" tibia whilst the portion of the tibia Ti which is remote relative to the femur F and/or adjacent to the ankle, not shown, is referred to as the "distal" tibia.

Figure 2:
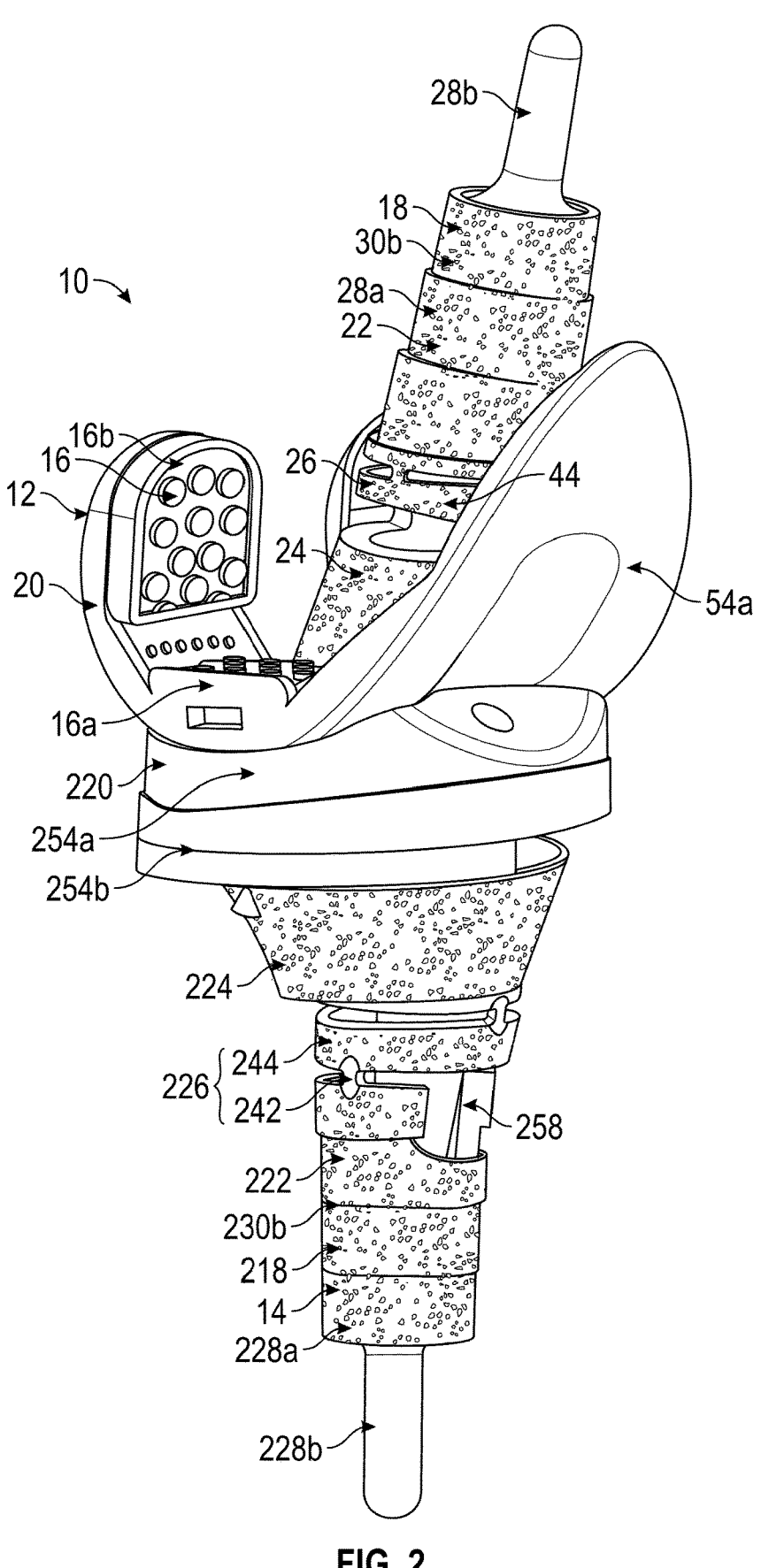
FIG. 2 shows a perspective representation of an embodiment of a rTKR including two revision-implant receivers in accordance with the first aspect of the invention, and two implants each having an implant anchor in accordance with the second aspect of the invention, in an assembled condition, with the bones omitted for clarity.

Referring now to FIG. 2, there is shown a revision joint replacement, indicated generally at 10 in an assembled condition. More specifically, the replaced joint is a knee such that FIG. 2 shows a revision prosthetic knee or revision knee replacement. The revision knee replacement in the present embodiment comprises both a femoral component 12 and a tibial component 14, such that the revision joint replacement 10 is a full revision prosthetic knee or revision Total Knee Replacement, hereon referred to as rTKR. The rTKR is to replace a failed first full prosthetic knee or primary Total Knee Replacement, hereon referred to as pTKR.

The femoral component or femoral construct 12 is associated with the femur, not shown in FIG. 2. The femoral component 12 comprises one or more augments 16, a revision-implant receiver 18, and an implant 20, although any of the first two features may be omitted. As the bone is the femur, the revision-implant receiver 18 may be said to be a femoral receiver and the implant 20 may be referred to as a femoral implant.

Figure 3:
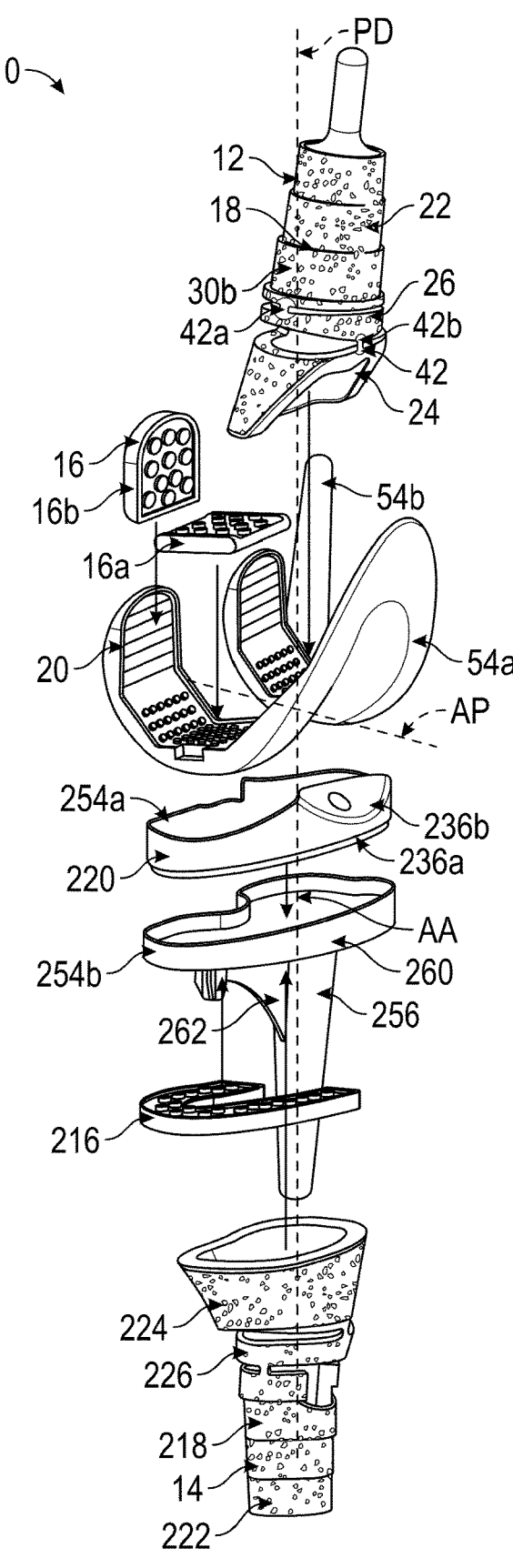
FIG. 3 shows an exploded perspective representation of the rTKR of FIG. 2.

If provided, at least one augment 16 enables linear adjustment of the position of the implant 20 relative to the femur along the proximal-distal axis or direction PD, indicated as a dotted line in FIG. 3. Such augments 16 are known as distal augments 16a. Alternatively or additionally, at least one augment 16 enables linear adjustment of the position of the implant 20 along the anterior-posterior axis or direction AP, indicated as a dotted line in FIG. 3. Such augments 16 are known as posterior augments 16b. The or each augment 16 is positioned between the bone and an appropriate inner face of a bearing surface of the femoral implant 20. Each augment 16 may be between 0.5 mm and 10 mm thick, and preferably is 5 mm thick. Each femoral augment 16 is stackable with a further femoral augment 16.

Figure 4:
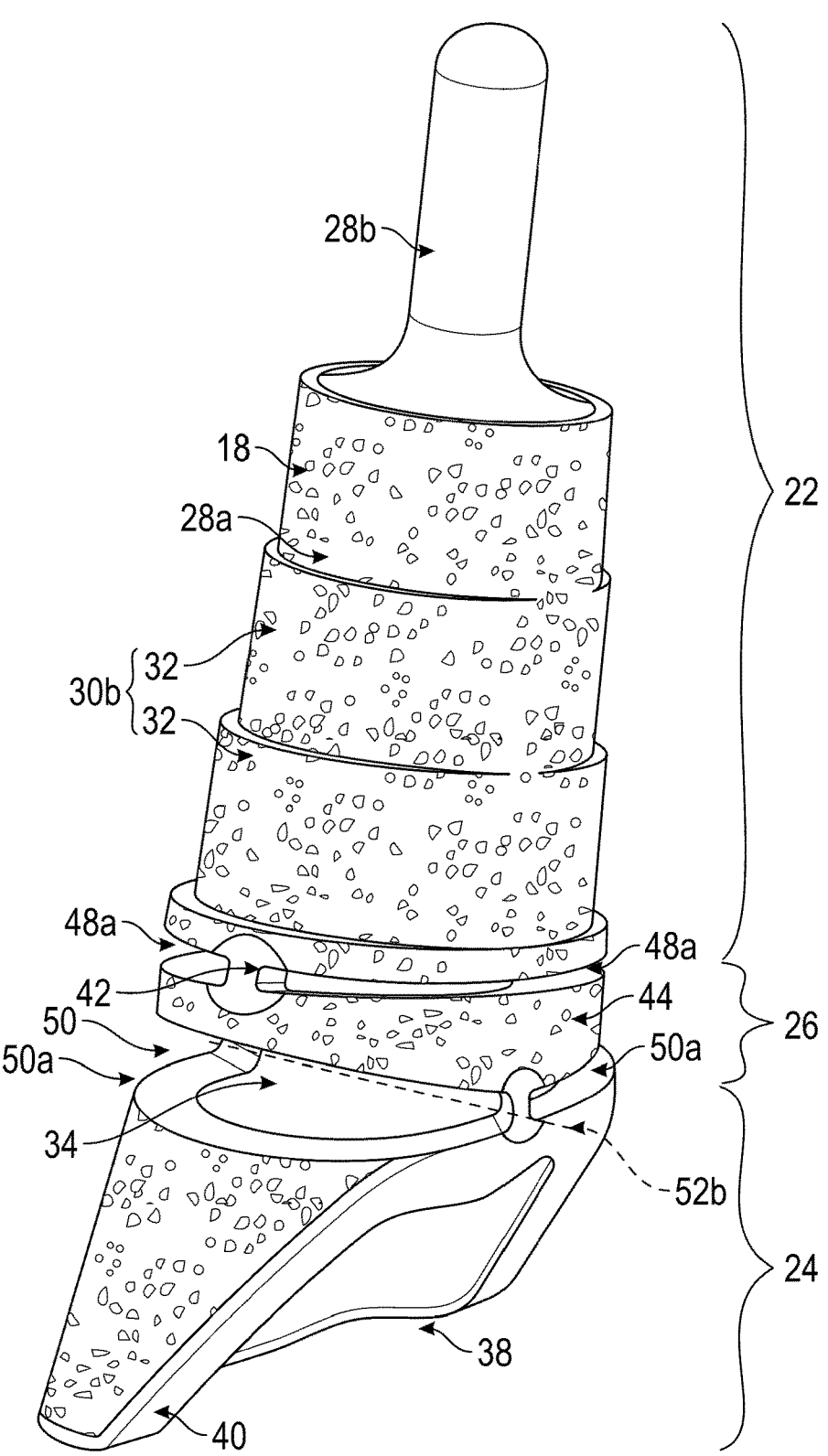
FIG. 4 shows an enlarged perspective representation of a femoral revision-implant receiver of FIG. 2.
Figures 5, 6:
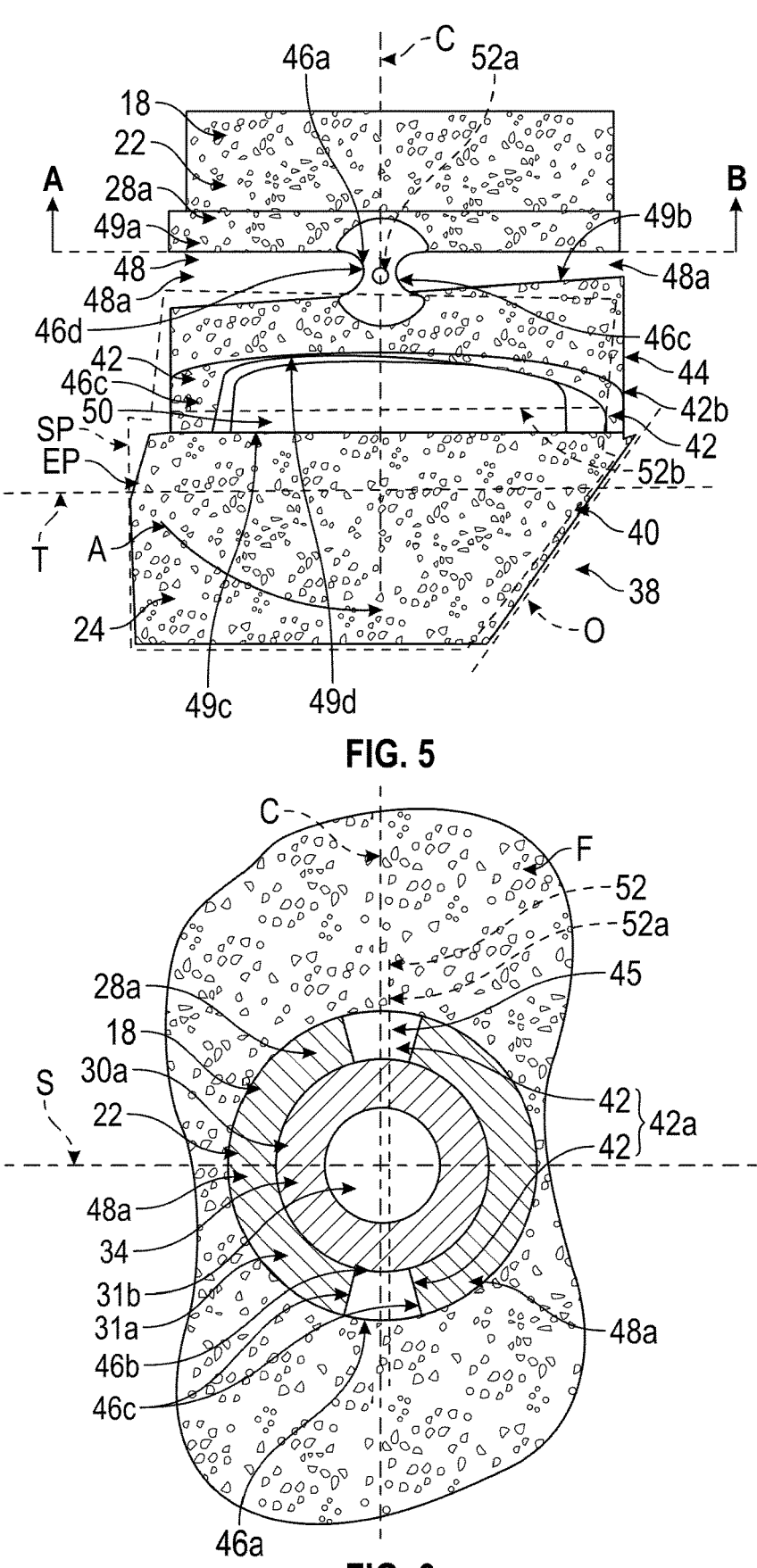
FIG. 5 shows an enlarged side view of a hinge element of the revision-implant receiver of FIG. 4.
FIG. 6 shows a cutaway below view along the line AB of the revision-implant receiver of FIG. 5, with the femur shown for clarity.

The revision-implant receiver or receiver 18, shown in FIG. 4, provides a strengthening structure or interface with the bone. The revision-implant receiver 18 is receivable within the intramedullary canal, which may need to be widened to accommodate the revision-implant receiver 18. The revision-implant receiver 18 also supports, engages, holds, or receives part of the femoral implant 20. In particular, the revision-implant receiver 18 distributes any loads or forces applied by or transmitted through the implant 20 across a greater area of the interface with the bone. Without the revision-implant receiver 18, any forces applied by the implant 20 may be concentrated to a point or small area of contact with the bone. This would lead to a higher risk of failure of the revision implant replacement 10, particularly where the bone is already fragile, damaged and/or deformed. As best shown in FIG. 4, the revision-implant receiver 18 comprises a first receiver element 22, a second receiver element 24 and a hinge element 26, a close-up view of which is shown in FIG. 5.

The first receiver element 22 is the part of the revision-implant receiver 18 which is inserted first into the bone. The first receiver element 22 may be referred to as a first portion, a sleeve, a cone, a proximal cone or sleeve, a proximal metaphyseal cone or sleeve, or a proximal diaphyseal cone or sleeve. The first receiver element 22 is preferably received in or positioned within at least the epiphysis. However, metaphyseal fixation may have to be considered where the epiphyseal bone stock is inadequate, or the bone quality is too poor to enable fixation thereat. In this case, the first receiver element 22 may need to be inserted into the metaphysis. The first receiver element 22 may even need to be at least partly or fully received within the diaphysis if the metaphyseal bone is too damaged. Metaphyseal fixation is preferred as it is less invasive than diaphyseal fixation, replicates natural bone loading more closely and retains diaphyseal bone stock if further revision is required.

The first receiver element 22 extends in-use along the proximal-distal axis PD of the bone. Preferably, the first receiver element 22 is integrally formed with the hinge element or hinge 26, and more preferably as a one-piece. The first receiver element 22 has a sleeve body 28a and, preferably, a receiver-stem portion or mini-stem 28b, integrally formed with, connected, or connectable with the sleeve body 28a at an end thereof. The sleeve body 28a is preferably hollow, for receiving at least part of the implant 20.

An inner surface 30a of the sleeve body 28a may be smooth or substantially smooth, although alternatives may include non-smooth, textured, or coated, for example, for increased friction. The inner surface 30a may have a, preferably continuous, side wall 31a and a base end 31b. Said base end 31b is preferably flat although concave, parabolic, curved, non-curved, part curved, conical, planar, polygonal or any other desirable geometry may be envisioned. The inner surface 30a in longitudinal cross-section may be considered to be a truncated cone, and more preferably is or is substantially frustoconical. In a further modification, however, one or both of the planar base end and the opposing open end of the inner surface may be non-parallel with each other and/or non-perpendicular to the proximal-distal axis PD in any desirable combination.

An outer surface 30b of the sleeve body 28a may have one or more steps or stepped portions 32. These steps 32 help with fixation, for instance via Morse fixation. Furthermore, the outer surface 30b may be coated with a suitable material to encourage bone growth.

As the average width or diameter of the sleeve body 28a preferably decreases monotonically towards the receiver-stem portion 28b, the first receiver element 22 can be generally considered to have at least a single taper, and more preferably to have a double taper or substantially double taper towards the receiver-stem portion 28b. In other words, the first receiver element 22 may be considered to be generally shaped as any of: a cone, a cone which may flare, a trumpet, and a frustrum of a cone. The first receiver element 22 may be symmetrical in the sagittal plane S and/or the coronal plane C but it could be envisioned that the first receiver element may be symmetrical in only one of the above planes, symmetrical in another plane altogether or even may have no symmetry. The first receiver element 22 and/or one or both the inner surface 30a and the outer surface 30*b* thereof is preferably circular in lateral or transverse cross-section or cut-away plan view, as best shown in FIG. 6, although non-circular alternatives may be envisioned. Alternative cross-sections include elliptical, ovoid, lachrymiform, curved, non-curved, part curved, polygonal, such as a square, rectangular, hexagonal, octagonal, a polygon having one or more chamfered and/or rounded corners, a polygon having one or more curved edges, any other suitable cross-section, or any combination thereof. FIG. 6 additionally shows the femur F.

When the first receiver element 22 is received within the bone, the first receiver element 22 is positioned and/or orientated such that the receiver-stem portion 28*b* may be positioned on, along or adjacent to a longitudinal, preferably central, axis or line of the intramedullary cavity. The "tip" of the first receiver element 22, or smaller base of the frustum and/or, here, the receiver-stem portion 28*b* is oriented towards, extends in or towards the diaphysis of the bone, and/or towards the metaphysis and/or epiphysis of the opposing end of the bone. In other words, the first receiver element 22 tapers to a mid-point of the long bone shaft.

The second receiver element 24 is the part of the revision-implant receiver 18 which is inserted second into the bone. The second receiver element 24 may be referred to as a second portion, a cone, a sleeve, a distal cone or sleeve, a metaphyseal cone or sleeve, or a distal epiphyseal cone or sleeve. The second receiver element 24 is engageable or engaged via the hinge element 26 with the first receiver element 22. Preferably, the second receiver element 24 is integrally formed with the hinge element 26 and/or the first receiver element 22. The second receiver element 24 is hollow. The hollow first receiver element 22 and the hollow second receiver element 24 define together a central cavity 34 for receiving part of the implant 20 therein. The second receiver element 24, the hinge element 26 and/or the central cavity 34 may be circular in lateral cross-section, at least at or adjacent to the first receiver element 22 and/or hinge element 26, although non-circular may be envisioned. Alternative lateral or transverse cross-sections of the central cavity may include elliptical, ovoid, lachrymiform, curved, non-curved, part-curved, polygonal, such as a square, rectangular, hexagonal, octagonal, having one or more chamfered or rounded corners and/or one or more curved edges, or any other suitable cross-section. The cross-section of the central cavity may change along the proximal-Distal axis PD although this feature may be omitted. The first receiver element 22 and/or the hinge element 26 may comprise, in lateral cross-section, a major dimension and a minor dimension. As the first receiver element 22 and/or hinge element 26 are preferably circular in lateral cross-section, the major dimension is the same as the minor dimension, and both correspond to a diameter.

The second receiver element 24 is or is substantially a trapezium in cross-section in the coronal plane C, indicated as a dashed line in FIGS. 5 and 6, although non-trapezium cross-sections in the coronal plane C may be envisioned, such as trapezoid, curved, non-curved, part-curved, linear, or any other desirable polygonal shape, whether regular, irregular, truncated or chamfered may be considered. The trapezium may be regular, irregular, or truncated. One or both legs or lateral sides of the trapezium may even be curved. In other words, the second receiver element 24 tapers towards the hinge element 26 along the proximal-distal axis PD. Furthermore, in lateral or transverse cross-section, an inner face and an outer face of the second receiver element 24 may be the same, or substantially the same as each other, or they may differ from each other. The second receiver element 24 and/or one or both of the inner and outer face of the second receiver element 24 may be any of: circular, non-circular, an ellipse, an oval, an ovoid, a flattened oval, a flattened ellipse, and square or a rectangle with at least one and up to four rounded edges and/or rounded corners, fabiform, reniform, an hourglass-shape, a figure of eight, an ellipse having one or more waisted sections, or any other desirable cross-sectional shape. The transverse plane T is illustrated as a dotted line in FIG. 5. The cross-section of the second receiver element may even change along the proximal-distal axis PD. Similarly to the first receiver element 22, the second receiver element 24 and/or the central cavity 26 may comprise in lateral cross-section a major dimension and a minor dimension. As the second receiver element 24 and/or the central cavity 26 are preferably circular in lateral cross-section, the major dimension is the same as the minor dimension, and both correspond to a diameter.

The second receiver element 24 is also truncated or chamfered, optionally along a plane. Said plane may be oblique plane O which is perpendicular to the sagittal plane S. The oblique plane O is angled relative to the coronal plane C, and more preferably is non-perpendicular and non-parallel thereto. The oblique plane O is also angled relative to the transverse plane T, and more preferably is non-perpendicular and non-parallel thereto. In other words, the oblique plane O preferably forms an acute angle with one or both of the coronal plane C and the transverse plane T. The oblique plane O and coronal plane C are shown as dashed lines in FIG. 5. The coronal plane C and the sagittal plane S are shown as dashed lines and dash-dot-dot lines respectively in FIG. 6. The femoral implant 20 comprises an inner face 36*a*, shown in FIG. 7 and the truncation or chamfer 38 enables the second receiver element 24 to be engageable with the inner face 36*a*. In particular, an increased contact area 40 is provided by the chamfer 38, best shown in FIGS. 4 and 5, which in-use prevents or inhibits any undesirable rotation of the femoral implant 20 around its longitudinal axis. In other words, the in-use contact area 40 due to the chamfer or truncation 38 engages with an inner surface 36*a* to prevent or inhibit the femoral implant 20 from "rolling" inside the revision-implant receiver 18.

The hinge element 26 enables the second receiver element 24 to be re-orientable, angularly adjustable, or bendable relative to the first receiver element 22. The hinge element 26 comprises at least one linking portion 42. Preferably as shown, the hinge element 26 comprises two pairs of linking portions 42, referred to as a first pair 42*a* and a second pair 42*b* for clarity, but it could be envisioned that either pair may be omitted or that more pairs may be provided. The hinge element 26 also comprises a spacer segment 44 but this feature may be omitted, or more than one spacer segment may be provided.

Each linking portion, link, connector, or hinge section 42 functions as a hinge or hinge section. As such, each linking portion 42 may be said to be bendable or deformable. More specifically, each linking portion 42 may be a live hinge, a living hinge or a hinge which is integrally formed as a one piece in the present embodiment. At least one linking portion 42, and preferably the first pair 42*a* connects or joins the first receiver element 22 and the spacer segment 44. Alternatively or preferably additionally, at least one linking portion 42, and preferably the second pair 42*b* connects or joins the second receiver element 24 with the spacer segment 44. In other words, the components of the revision-implant receiver 18 are connected in the following order: the first receiver element 22, the first pair 42*a* of linking portions 42, the spacer segment 44, the second pair 42b of linking portions 42, and second receiver element 24. Each linking portion 42 and/or each pair of linking portions 42a,42b may be connectable, connected, or here, integrally formed with the spacer segment 44 and/or one of the first receiver element 22 and the second receiver element 24. In the present embodiment, all the above components are preferably integrally formed with each other as a one piece for ease of manufacture and/or strength, but this feature may be omitted. The receiver 18 or parts thereof may be formed by extrusion and/or moulding. The receiver may even be formed in a bent orientation from the onset, or be bent secondarily.

As shown, each linking portion 42 comprises at least one strip or pillar 45. Each linking portion 42 has four linking surfaces: an outward-facing surface 46a, an inward-facing surface 46b and two lateral surfaces 46c. Each linking portion 42 has a rectangular or square in lateral cross-section, but may alternatively be curved, non-curved, part-curved, circular, non-circular, or polygonal, such as hexagonal or octagonal, whether regular, irregular, truncated, or chamfered in lateral, latitudinal or transverse cross-section, and/or may have fewer or more linking surfaces. The outward-facing surface 46a faces or abuts against the bone whilst the inward-facing surface 46b faces inwards, i.e. towards the central cavity 34. The outward-facing surface 46a is convex in transverse cross-section, whilst the inward-facing surface 46b is concave in lateral or transverse cross-section as best shown in FIG. 6, although either or both surfaces may be convex, concave, planar or substantially planar or any other suitable geometry.

Each linking portion 42 also preferably comprises a waisted portion 46d, also referred to as a waist or an hourglass shape, for enabling bending. The waisted portion 46d is defined as a portion of the linking portion 42 which extends at least partway along the proximal-distal extent of the linking portion and which comprises a minimum in the transverse or lateral cross-sectional area of the linking portion 42. In other words, each linking portion 42 has a narrower cross-section, or minimum width, cross-sectional area or lateral extent. Said minimum width may be equidistant or substantially equidistant from the spacer segment 44 and the relevant receiver element 22,24, as this may provide the greatest range of angular adjustment possible. The waisted portion 46d is provided by at least one of the lateral surfaces 46c or part thereof being concave or having an indent. The indent may be curved and/or linear in longitudinal cross-section. Preferably, both lateral surfaces 46c of a linking portion 42 are concave or have a concave section such that the concave lateral surfaces 46c are on opposing sides of each linking portion 42.

Preferably the revision-implant receiver 18 comprises a material which is simultaneously strong and/or rigid, whilst being pliable, bendable or deformable at the waisted portion 46d without any risk of structural failure or with a reduced likelihood of structural failure. The rTKR or any part thereof may comprise plastics, ceramics, metal, glass, or any combination thereof. Preferably, the revision-implant receiver 18 is formed of one or more metals, such as titanium, cobalt, or chromium, or an alloy, although any suitable material may be considered. The rTKR or any part thereof is preferably solid.

In addition to functioning as a hinge, each linking portion 42 preferably has a spacing function. Each linking portion 42 may therefore also be referred to as a divider, a bridging element, a bridge, or a spacer. In particular, at least one linking portion 42, and more preferably the first pair 42a of linking portions 42 spaces apart the first receiver element 22 from the spacer segment 44 along the longitudinal direction or proximal-distal axis PD to provide a gap therebetween, referred to for clarity as a first gap 48. The first pair 42a of linking portions 42 delimitates the first gap 48 into two first sub-gaps or first hollows 48a. The first receiver element 22 has at least one first rim or rim surface 49a, as shown in FIG. 5. The first rim 49a faces the spacer segment 44 and/or the second receiver element 24. Preferably, the first rim 49a defines at least in part the first gap 48. Preferably, the spacer segment 44 has a similar spacer rim 49b which faces the first rim 49a, also shown in FIG. 5.

Similarly, at least one linking portion 42, and more preferably the second pair 42b spaces apart the second receiver element 24 from the spacer segment 44 to provide a gap therebetween, referred to for clarity as a second gap 50. The second gap 50 may be divided into two second sub-gaps or second hollows 50a by the second pair 42b of linking portions 42. The second receiver element 24 has at least one second rim or rim surface 49c. The second rim 49c faces the spacer segment 44 and/or the first receiver element 22. Preferably, the second rim 49c defines at least in part the second gap 50. Preferably, the spacer segment 44 has a similar spacer rim 49d which faces the second rim 49c, also shown in FIG. 5. Any of the rims 49a,49b,49c,49d may be planar and/or non-planar.

Each linking portion 42 of a pair is preferably positioned on either side of the central cavity 34, as best shown in FIG. 6. Each linking portion 42 and/or each pair of linking portions 42 has or defines an axis of bending or rotation, referred to as a hinge axis 52. For clarity, the hinge axes 52 defined by the first pair 42a and the second pair 42b may be referred to as the first hinge axis 52a and the second hinge axis 52b respectively. The first hinge axis 52a is illustrated in FIG. 5 as a dot as the first hinge axis 52a goes into the page, and as a dotted line in FIG. 6. The second hinge axis 52b is illustrated a dotted line in FIGS. 4 and 5. Any further hinge axes in alternative embodiments would have a similar distinguishing incremental numbering.

The direction or orientation of the or each hinge-axis 52 is determined by the relative positions and/or orientation of the concave lateral surfaces 46c and/or of the relative position of the linking portions of a pair. The or each hinge axis 52 may extend across or span a major or minor dimension of the central cavity 34. As the first receiver element 22 and/or the second receiver element 24 preferably has a circular cross-section, at least at or adjacent to the hinge element 26, the or each hinge axis 52 preferably extends diametrically across or spans the diameter of the central cavity 34, as shown in FIG. 6. In other words, the or each hinge axis 52 is along, on or parallel to a diameter of the first receiver element 22 and/or the second receiver element 24.

Preferably, the first hinge axis 52a extends in the coronal plane C, preferably in a medial-lateral direction for enabling angular adjustment of the second receiver element 24 relative to the first receiver element 22 in the anterior-posterior plane or sagittal plane S, as shown in FIG. 6. Alternatively, the first hinge axis 52a may extend in the sagittal plane S, preferably in an anterior-posterior direction for enabling angular adjustment of the second receiver element 24 relative to the first receiver element 22 in the medial-lateral plane or coronal plane C. In this latter case, by mechanical necessity, the spacer segment 44, if provided, is also rotated in the coronal plane C. It may be envisioned that either or both axes may extend in any other suitable plane.

The second hinge axis 52*b* is preferably non-parallel with the first hinge axis 52*a* to enable angular re-orientation in two distinct planes. More preferably, the second hinge axis 52*b* is perpendicular with the first hinge axis 52*a*.

The spacer segment 44 connects, at least indirectly, the first receiver element 22 and the second receiver element 24 and is preferably positioned therebetween. The spacer segment 44 may also be referred to as a mounting element or mounting body. As the spacer segment 44 is engaged with the first receiver element 22 by the first pair of bendable linking portions 42, and with the second receiver element 24 by the second pair of bendable linking portions 42, the second hinge axis 52*b* is spaced-apart from the first hinge axis 52*a* by the spacer segment 44 along the longitudinal or proximal-distal axis PD of the revision-implant receiver 18.

Figure 6A:
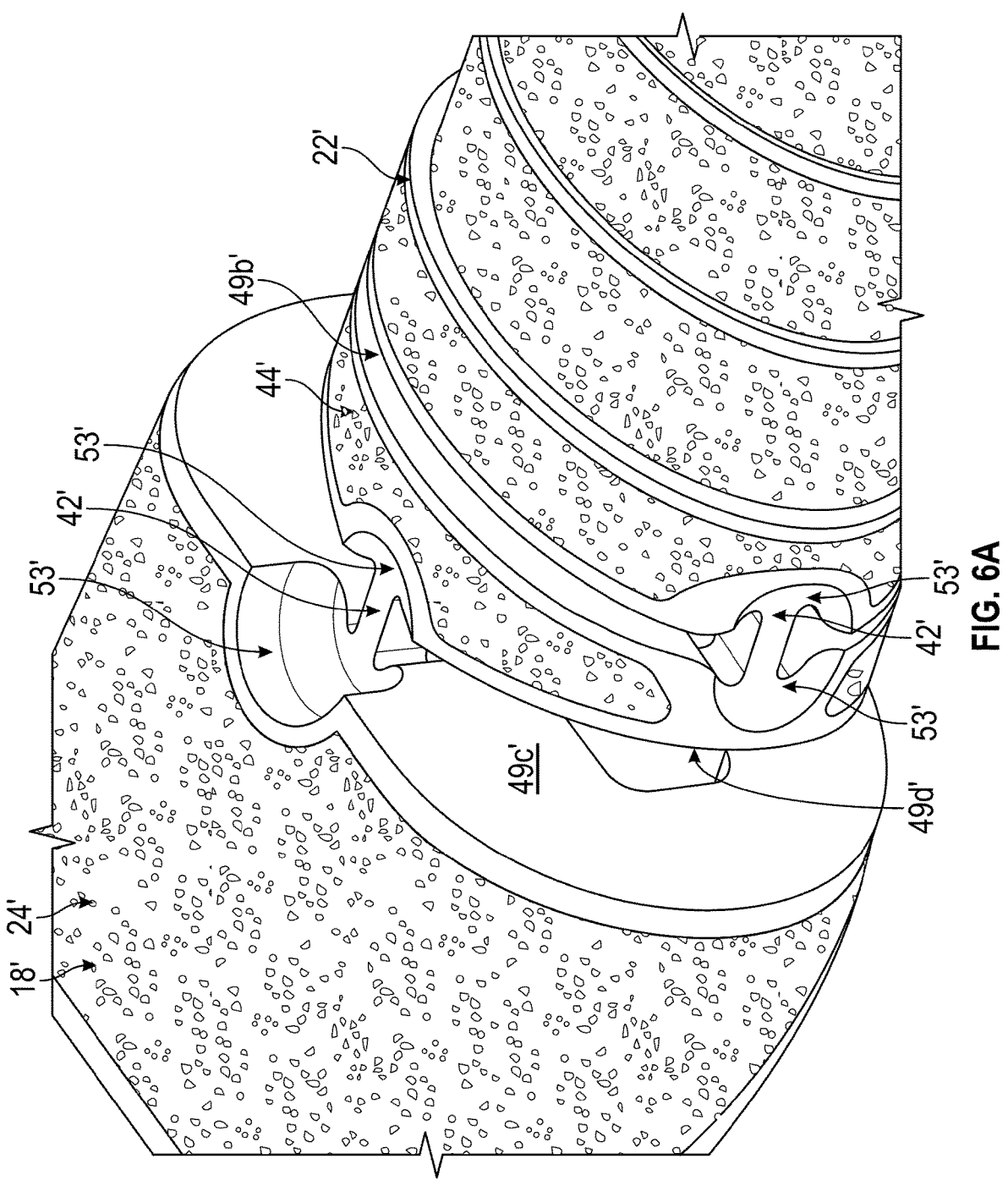
FIG. 6A shows a partial perspective view of a further embodiment of a revision-implant receiver.

FIG. 6A shows a partial perspective view of an alternative embodiment of a receiver 18'. The alternative embodiment of the receiver 18' is similar to the receiver 18 of the first embodiment. Detailed description of the common features is omitted for brevity. The caveats of the first embodiment apply to the present embodiment. Features of the alternative embodiment of the receiver 18' which are the same or similar to features of the receiver 18 have the same or similar reference numerals with an apostrophe added as a suffix.

The second receiver element 24' is or is substantially an ellipse in transverse cross-section at or adjacent the hinge element 26'. The spacer segment 44' and/or the first receiver element 22' is or is substantially circular in cross-section. The long diameter of the ellipse is preferably greater than a diameter of the spacer segment 44' and/or of the first receiver element 22', but a same or smaller long diameter may be an option. The short diameter of the ellipse may be the same or greater than the diameter of the diameter of the spacer segment 44' and/or the first receiver element 22', but smaller may be an option.

Figure 6B:
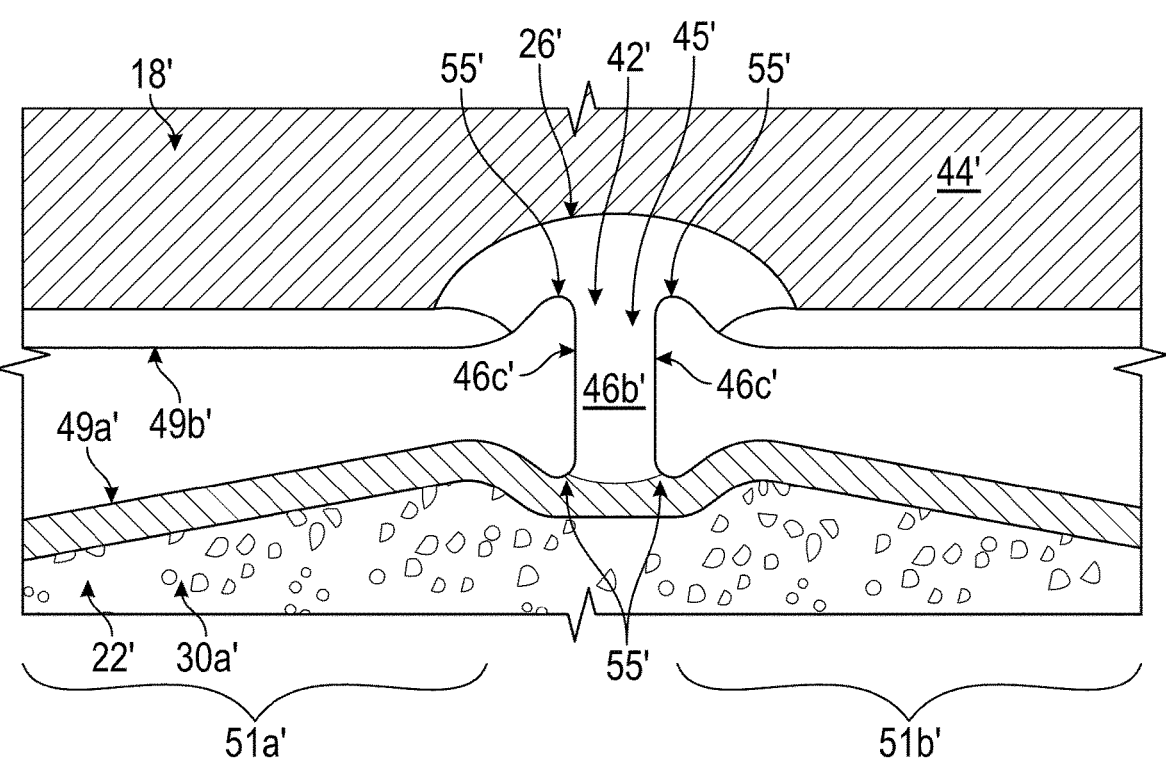
FIG. 6B illustrates a close-up side view of a hinge element of FIG. 6A.
Figure 6C:
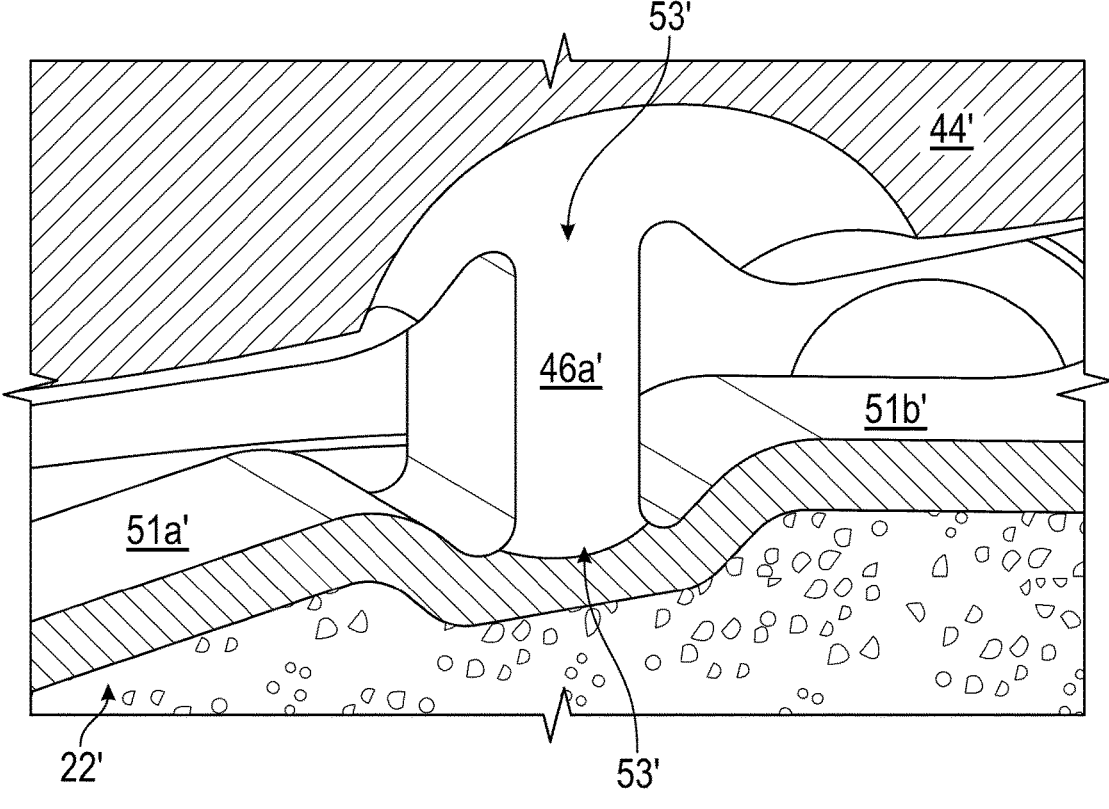
FIG. 6C is a further close-up perspective view of the hinge element of FIG. 6A.

The alternative embodiment of the hinge element 26' is similar to the hinge element 26, having at least one linking portion 42', and optionally at least one spacer segment 44'. Detailed description of the common features is omitted for brevity. FIG. 6B shows a close-up of part of the hinge element 26' or part thereof, viewed from within the receiver 18'. FIG. 6C shows the close-up of the same hinge element 26' or part thereof, viewed from outside the receiver 18'. More preferably, FIGS. 6B and 6C illustrate a linking portion 42' between the first receiver element 22' and the spacer segment 44'.

Each linking portion 42' between the second receiver element 24' and the spacer segment 44' is preferably similar to the linking portions 42' between the first receiver element 24' and the spacer segment 44' of the alternative embodiment. Detailed description of the common features is omitted for brevity. It could easily be envisioned, however, that any of the linking portions may be the same as the linking portions of the first embodiment.

Similarly to the first embodiment of the linking portion 42, each linking portion 42' comprises at least one strip, beam or pillar 45'. Each linking portion 42' has four linking surfaces: an outward-facing surface 46*a'*, an inward-facing surface 46*b'* and two lateral surfaces 46*c'* in the shown embodiment but any alternative number of linking surfaces may be provided. Each linking portion 42' preferably has a rectangular or square in lateral, transverse and longitudinal cross-section, but non-rectangular or non-square cross-sections, whether lateral, longitudinal and/or transverse, may be envisioned. In addition to functioning as a hinge, each linking portion 42' preferably has a spacing function. Each linking portion 42' may therefore also be referred to as a divider, a bridging element, a bridge, or a spacer. The same caveats for the linking portion 42 of the first embodiment apply here.

Unlike the first embodiment of the linking portion 42, each linking portion 42' of the further embodiment is preferably devoid of a waisted portion, although this alternative may easily be envisioned. In other words, each linking portion 42' preferably has a constant or substantially constant cross-section, or width, cross-sectional area or lateral extent along its longitudinal extent. Any and preferably all the lateral surfaces 46*c'* are or are substantially planar, but non-planar may be an option, such as curved or part curved longitudinally and/or laterally.

In the further embodiment, the first rim 49*a'* is at least in part non-planar and/or does not extend in only one plane, but this is optional. As shown in FIGS. 6B and 6C, the first rim 49*a'* on either side of the linking portion 42' has at least one, and preferably two rim sub-portions 51*a'*,51*b'*. Each of the two rim sub-portions 51*a'*,51*b'* is preferably planar along both the longitudinal extent and the width or radial extent of the first rim 49*a'* but non-planar, such as curved, along either or both extents may be an option. Each rim sub-portions 51*a'*,51*b'* is preferably angled, such that the rim sub-portions 51*a'*,51*b'* are non-coplanar and non-parallel with each other. Preferably, the two rim sub-portions 51*a'*,51*b'* are angled towards the linking portion 42' and/or towards the spacer segment 44'. The longitudinal extent of the linking portion 42' and each rim sub-portions 51*a'*,51*b'* may be considered to form a, preferably obtuse, angle. The angle is preferably between 90° and 180°, more preferably between 95° and 150°, and even more preferably is between 100° and 120°.

The spacer rim 49*b'* has no such non-coplanar rim sub-portions but in an alternative embodiment, optionally non-coplanar and/or non-parallel rim sub-portions may be provided. The spacer rim 49*b'* is preferably planar but non-planar is an option. The spacer rim 49*b'* preferably extends in a single plane.

The second rim 49*c'* is preferably planar as clearly shown in FIG. 6A, similarly to the spacer rim 49*b'* but non-planar may be an option. The spacer rim 49*d'* preferably comprises rim sub-portions, similarly to the first rim 49*a'* but these may be omitted.

The hinge element 26' preferably further comprises at least one recessed portion 53'. In total, the hinge element 26' has eight recessed portions 53'. The recessed portions 53' are recessed along a longitudinal direction of the receiver 18'. In other words, the recessed portions 53' are recessed in longitudinal cross-section. At least one, and more preferably two such recessed portions 53' are provided in at least one of, and more preferably each of the rims 49*a'*,49*b'*,49*c'*,49*d'*. A first said recessed portion 53' in FIG. 6B is preferably provided where the rim sub-portions 51*a'*,51*b'* would meet, but this is optional. One or both rim sub-portions, if provided, preferably continuously transition into the recessed portion 53' without forming an edge as shown, but this alternative may be an option for one or both rim sub-portions. The linking portion 42' extends from the recessed portion 53' towards to the spacer segment 44'. At least one of and preferably each of the outward-facing surface 46*a'*, the inward-facing surface 46*b'* and two lateral surfaces 46*c'* of the linked portion 42' meets with the recessed portion 53' without forming any edge or groove, although this alternative may be an option for one, all or any of the surfaces.

Furthermore, in FIG. 6B, a second of the previously mentioned recessed portions 53' is provided in the spacer rim 49*b'*. Similarly to the first said recessed portion 53', each lateral surface 46*c'* meets with the second said recessed portion 53' without forming any edge or groove, although this alternative may be an option for one, both or each lateral surface. Therefore, the linked portion 42' continuously transitions into both recessed portions 53'. In yet again other words, the junction 55' between any surface 46a',46b',46c' and a said recessed portion 53' may be curved. The linking portion 42' may thus be considered to be a beam or pillar with radiused ends.

The advantage of the linking portion 42' connecting with the recessed portions 53' is that the linking portion 42' may be more elongate, or at least more elongate than the height of the relevant gap and/or than a linking portion 42 of the first embodiment. An elongate linking portion 42' may provide a better distribution of the forces, such as the stress forces acting on the linking portion 42', and consequently a better distribution of the bending. Furthermore, the waisted portion of the first embodiment may be a stress raiser, stress riser, or stress concentration. Thus, although a waisted portion may be easily provided, having a constant or substantially constant cross-section in the present embodiment may further improve the distribution of forces as the stress forces are not localised to the narrower, waisted portion of the first embodiment. Instead, the forces may be distributed along the longitudinal extent of the linking portion 42'. In turn, a better distribution of forces may result in a lower risk of structural failure.

Similarly, the curvature of the junctions where the linking portion surfaces meet the recessed portions 53' may also distribute the forces acting on the linking portion 42'. In other words, the forces acting on the linking portion 42' are not localised to an edge. Thus, each junction 55' between the first receiver element 22' and the spacer segment 44' is not a stress raiser.

Alternatively or, preferably, additionally to recessing along the longitudinal direction, the, each or at least one said recessed portion 53' may also be recessed in a radial direction or transverse cross-section, as most clearly shown in FIG. 6A, relative to the outer and/or inner surfaces of the receiver 18'. Each recessed portion 53' may optionally form an edge with the relevant inward-facing and/or outward-facing surface of either or both the first and second receiver elements, but a continuous transition, such as curved, part curved or planar transition may be envisioned. Each recessed portion 53' continuously transitions into the relevant outward-facing surface 46a' and/or inward-facing surface 46b' of the linking portion 42', preferably without forming an edge. The transition may be planar, part planar, non-planar or curved.

Preferably, the inward-facing surface 46b' is flush to the inner surface 30a' and/or to an inner surface of the spacer segment 44', but could be non-flush, such as recessed and/or projecting beyond either inner surface in an alternative embodiment. In other words, in an alternative embodiment, the said recessed portion, the linking portion or both may be recessed radially inwardly relative to an inner surface of one or both the first receiver element and second receiver element. As recessed radially inwards relative to the inward facing surface of the receiver, the inward-facing face of the recessed portion and/or linking portion may be considered to be outward relative to the inward-facing surface of either or both receiver elements along a direction from within to outside the receiver on a transverse plane. However, the outward-facing surface 46a' is preferably non-flush to the outer surface 30b' and/or to an outer surface of the spacer segment 44', but could be flush or projecting beyond either outer surface. This is most clearly shown in FIG. 6A. More preferably, the outward-facing surface 46a' is recessed radially or in transverse cross-section relative to either or preferably, both outer surfaces. In other words, an outer or outwardly-facing surface of one or both the linking portion and the said recessed portion may be recessed radially inwardly relative to an outer surface of one or both the first receiver element and second receiver element. As recessed radially inwards relative to the outward facing surface of the receiver, the outward-facing face of one or both of the recessed portion and the linking portion may be considered to be inward relative to the outward-facing surface of one or both receiver elements along a direction from within to outside the receiver on a transverse plane. If the recessed portion along the longitudinal extent is omitted, a linking portion recessed relative to the outward-facing and/or inward-facing surface of any of: the first receiver element, the second receiver element and the spacer segment, may form a continuous transition therewith, such as curved and/or without forming an edge, although these alternatives may be envisioned.

At least part of the relevant rims may preferably be solid and/or non-porous. This may further distribute forces and/or reduce the likelihood of a stress raiser, thereby reducing the risk of structural failure. In the shown embodiment, the receiver element 18' is at least in part porous and/or, preferably, has a porous coating, but this is optional. The porous coating is provided on the inner and/or outer surfaces of any or any combination of: the first and second receiver elements 22',24' and the spacer segment 44' but may be omitted from any or all surfaces. The porous coating may be plasma-sprayed and/or electrochemically deposited onto the relevant part of the receiver. The porous portion or porous coating and/or the receiver may be formed by Additive Manufacturing. The receiver and/or porous portion or coating may be formed from a solid billet which is machined into the desired shape and/or texture. The porous and non-porous parts may be formed of the same material and/or of different materials.

As shown, a portion of the first receiver 22' at or adjacent the first rim 49a' is solid and/or non-porous but this option may be envisioned. The depth of the solid portion is preferably less than 20 mm, but greater than 20 mm may be an option. More preferably, the depth is less than 10 mm and most preferably is 2 mm. Preferably, the spacer segment 44' is formed of solid and/or non-porous materials. Alternatively, any part of all of the receiver may be porous or solid.

Although the spacer rim 49b' is preferably planar, it may alternatively be envisioned that one or more rim subportions may be provided. The rim sub-portions may be planar or non-planar. The rim sub-portions may be non-angled or angled, such as non-coplanar and/or non-parallel. The rim sub-portions may be curved in longitudinal and/or lateral extent.

Whilst the linking portion in FIGS. 6B and 6C is between the first receiver element 22' and the spacer segment 44', the shown linking portion may alternatively be provided between the first receiver element and the second receiver element if no spacer segment is provided. Furthermore, although the hinge element 26' is shown as part of a revision-implant receiver, it may easily be provided in an implant.

Figure 7:
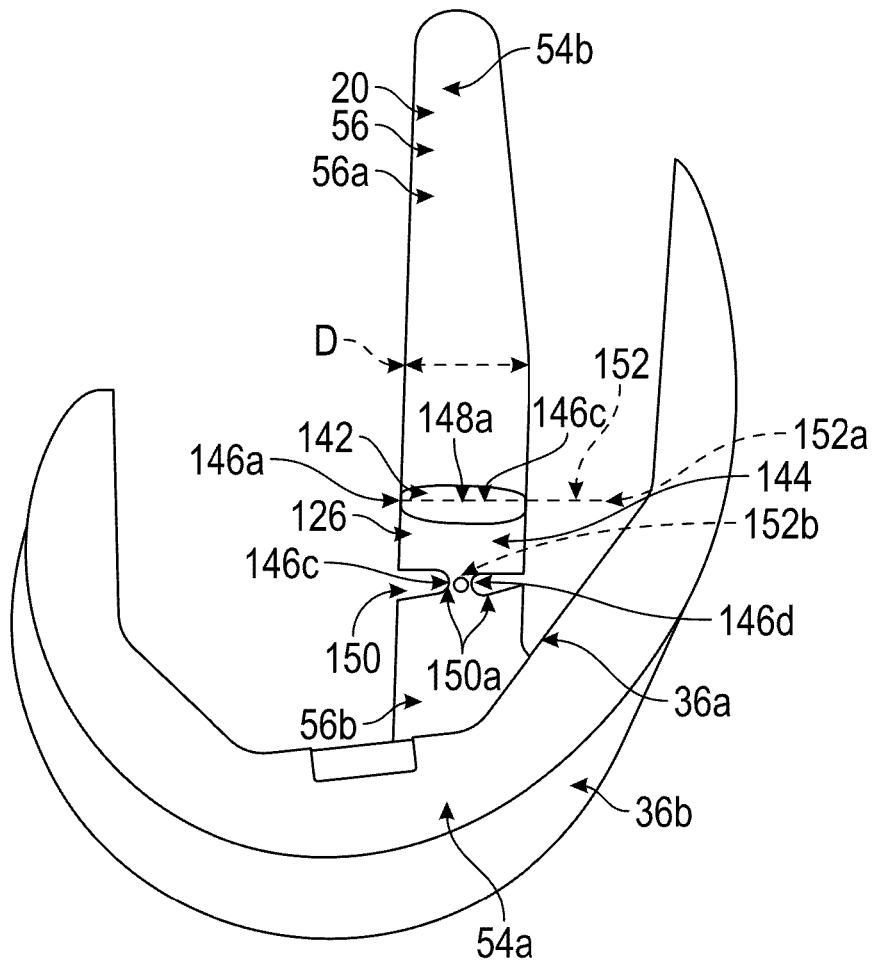
FIG. 7 shows a side view of a femoral implant of FIG. 2.

Referring now to FIG. 7, the femoral implant 20 comprises a bearing surface 54a and an implant anchor 54b. The femoral implant 20 may be formed of plastics, metal, ceramics, or a combination of the above. The femoral implant 20 of a rTKR may retain the same core dimensions, sides, and size ranges as a femoral implant of a pTKR equivalent.

The bearing surface 54a has the above-mentioned inner face 36a and an outer face 36b.

The inner face 36a is preferably planar, as shown in FIG. 7. Similarly, the contact area 40 is preferably also planar. In an alternative embodiment, it may be envisioned that the inner face and/or the contact area may be non-planar. The inner face and/or the contact area may have a curved cross-section in any of the sagittal plane S, the coronal plane C, the transverse plane T, or any combination thereof. The inner face and/or the contact area may be curved along at least one direction and/or dimension. In other words, the inner face and/or the contact area may be curved when viewed going into the page and/or in the plane of the page in FIG. 7 for the inner face, and in FIG. 5 for the contact area. The curved or radiused cross-section or cross-sections may comprise a circle arc, an ellipse arc, an ovoid arc, a parabola, or any other suitable curved cross-section, whether regular, or irregular. The curvature may be towards the stem or away therefrom in the case of the inner face and/or outwards or inwards in the case of the contact area. In other words, the inner face and/or the contact area may be convex and/or concave. The inner face and/or the contact area may comprise a portion of an area of a cylinder. The curvature may be limited to a portion of the inner face and/or a portion of the contact area.

The outer face 36b provides the face which articulates with or is engageable with the tibia or tibial component 14. Preferably, the bearing surface 54a does not comprise any pegs, such as the medial and lateral pegs, unlike a pTKR femoral component, although this alternative may be envisioned.

The implant anchor 54b supports, connects, joins, or engages with the bearing surface 54a. The implant anchor 54b comprises a first portion and a second portion which is hingeably engaged or engageable with the first portion. More specifically, the implant anchor 54b comprises a stem 56. The stem 56 has at least a first stem portion 56a, and preferably a first stem portion 56a and a second stem portion 56b. The second stem portion 56b is engaged or engageable via a hinge element 126 with the first stem portion 56a.

Features of the implant 20 which are similar to features of the revision-implant receiver 18 have similar reference numerals, with the prefix "1" added.

Preferably, the stem 56 is or is substantially circular, elliptical or a disc in cross-section along at least a majority of its longitudinal extent, although the stem may be circular, oval or a disc along a minority of its longitudinal extent. Alternative cross-sections may be considered such as oval, ovoid or lachrymiform. The stem 56 is full or non-hollow but may be hollow for weight considerations. Preferably, the stem 56 is connected to the bearing surface 54a by being integrally formed therewith, although connected or connectable by a connector may be envisioned. In other words, the stem 56 is preferably a fixed stem 56. This advantageously enables cemented fixation, which may be preferred to mechanical fixation. Furthermore, the fixed stem 56 may grow proportionally with implant size and/or may allow for a full range of angular adjustment within a compatible revision-implant receiver 18.

The first stem portion 56a is inserted or received first in the revision-implant receiver 18, whilst the second stem portion 56b is inserted or received second in the revision-implant receiver 18.

The hinge element 126 of the implant 20 is similar to the hinge element 26 of the revision-implant receiver 18, having at least one linking portion 142, at least one hinge axis, and at least one gap. Preferably, the hinge element 126 comprises two linking portions 142, each defining a hinge axis 152, a first said hinge axis 152a indicated as a dotted line in FIG. 7, a second said hinge axis 152b indicated as a dot in FIG. 7, a first gap, two first sub-gaps 148a, a second gap 150, and two second sub-gaps 150a, although any of the above, including the hinge element, may be omitted. Detailed description of the common features is omitted for brevity.

The or each linking portion 142 of the implant 20 is similar to each linking portion 42 of the revision-implant receiver 18, having similar material properties, an outward-facing surface 146a, two lateral surfaces 146c, and a waisted portion 146d. Detailed description of the common features is, once again, omitted for brevity.

As the stem 56 is preferably non-hollow, each linking portion 142 does not comprise an inward-facing surface. Instead, each linking portion 142 comprises two outward-facing surfaces 146a. As the stem 56 is preferably circular in cross-section, each linking portion 142 may be formed by extrusion or moulding. As such, each outward-facing surface 146a may be non-rectangular or non-square in side view or in front view. Instead, each outward-facing surface 146a may, in side view or in front view, have one or two edges which may be curved. Furthermore, the implant 20 does not require a pair of linking portions 142 to define a hinge axis 152, as one linking portion may suffice, unlike the revision-implant receiver 18, although nothing excludes a plurality of linking portions from defining the hinge axis. In the present embodiment, the or each hinge axis 152 is preferably defined by one linking portion 142. The or each linking portion 142 preferably extends along at least a major extent of a diameter D of the stem 56.

The hinge element 126 of the implant 20 optionally further comprises a spacer segment 144. The first said bendable linking portion 142 connects the spacer segment 144 to the first stem portion 56a. The second said bendable linking portion 142 connects the spacer segment 144 to the second stem portion 56b, although either of these features may be omitted. The second bendable linking portion 142 defines the second hinge axis 152b.

Similarly to the revision-implant receiver 18, the first said bendable linking portion 142 and the second bendable linking portion 142 are spaced-apart by the spacer segment 144. The second linking portion 142 provides the second gap 150 between the spacer segment 144 and the second stem portion 56b. Said second gap 150 is divided into the two second sub-gaps 150a. Preferably, the first hinge axis 152a and second hinge axis 152b of the implant 20 are non-parallel with each other for enabling angular adjustment of the bearing surface 54a in two distinct planes. The second hinge axis 152b may be perpendicular to the first hinge axis 152a. The first hinge axis 152a is preferably aligned with or contained within the sagittal plane S. The first hinge axis 152a more preferably extends in the anterior-posterior direction, thereby enabling rotation, re-direction or re-orientation of the second stem portion 56b relative to the first stem portion 56a in the coronal or medial-lateral plane. If provided, by mechanical necessity, the spacer segment 144 is also rotated relative to the first stem portion 56a in the coronal plane C. The second hinge axis 152b is aligned with or contained within the coronal plane C and preferably extends in the medial-lateral direction for enabling angular rotation in the sagittal plane S. The direction or orientation of the first and second hinge axes could easily be inverted in an alternative embodiment or may even not be contained within either of the coronal or sagittal planes, or any other reference plane.

Referring back to FIGS. 2 and 3, the tibial component or tibial construct 14 is associated with the tibia, not shown. The tibial component 14 comprises one or more augments 216, a tibial revision-implant receiver 218, and a tibial implant 220, although any of the first two features may be omitted.

Features of the tibial component 14 which are similar to features of the femoral component 12 have similar reference numerals with the prefix "2" added.

The or each tibial augment 216 is preferably shaped to at least partially surround the tibial implant 220 or part thereof. Each tibial augment 216 is stackable with a further tibial augment 216. Each augment 216 may be between 0.5 mm and 10 mm thick, and preferably is 5 mm thick.

The tibial revision-implant receiver 218 is similar to the femoral revision-implant receiver 18, having similar first receiver element 222, second receiver element 224, and tibial hinge element 226, sleeve body 228a, mini-stem 228b, outer surface 230b, coating, and manufacture although any of these features may be omitted. For brevity, detailed description of the common features is omitted. The first receiver element 222 of the tibial component 14 is distal, whilst the second receiver element 224 is proximal, unlike the femoral first and second receiver elements 22,24. As shown in FIGS. 2 and 3, the first receiver element 222 comprises an aperture, gap or opening 258 adjacent to the hinge element 226, but this feature may be omitted. Furthermore, the second receiver element 224 is preferably non-chamfered or non-truncated. The second receiver element 224 may be circular, non-circular, oval, elliptical, fabiform, reniform, or a cardioid in lateral or transverse cross-section, or any other desirable shape.

The tibial hinge element 226 is similar to the femoral hinge element 26, having similar at least one pair of linking portions 242, and preferably two pairs of linking portions 242, each defining a hinge axis, spaced-apart by a tibial spacer segment 244. Detailed description of the common features is again omitted for brevity.

The tibial implant 220 comprises a tibial bearing surface 254a and an implant anchor 254b, which are similar to the bearing surface 54a and the implant anchor 54b of the femoral component 12. Detailed description of the common features is yet again omitted for brevity. The tibial implant 220 of the rTKR may retain the same core dimensions, sides, and size ranges as a tibial component of a pTKR.

The bearing surface or bearing 254a has an inner face 236a and an outer face 236b. The tibial bearing 254a may be the same as or may even be the same tibial bearing in the primary knee. The outer face 236b provides the surface which articulates with or is engageable with the femoral component 12. The inner face 236a connects or engages with the implant anchor 254b, whether via a connector or, preferably being interference fit, although integrally formed therewith may be an option.

The implant anchor 254b supports, connects, joins, or engages with the bearing surface 254a. The implant anchor 254b comprises a stem 256 and a tibial plateau 260 which is engageable with the bearing surface 254a. More specifically, the bearing surface 254a or part thereof may be received on or in the tibial plateau 260, although integrally formed with the tibial plateau may be an option. The implant anchor 254b may optionally comprise a first connector portion and the bearing surface 254a may comprise a second connector portion, the first and second connector portions being complementarily engageable with each other, not shown.

Preferably, the stem 256 comprises a hinge or hinge element, not shown, along the longitudinal extent of the stem 256, but alternatively, the hinge element may be omitted, for instance if used with the revision-implant receiver. Alternatively or additionally, the stem may be connected or connectable with the tibial plateau, optionally hingeably, such as via a connector comprising first and second connector portions.

Preferably, the tibial plateau or tibial tray 260 is integrally formed with the implant anchor 254b and/or stem 256, but alternatives such as connected, connectable or separably connectable may be envisioned, to provide greater modularity. In other words, the rTKR tibial implant 220 may comprise a fixed stem 256, unlike a pTKR tibial component. The fixed stem 256 enables or provides for cemented fixation. Furthermore, the fixed stem 256 may grow proportionally with the size of the tibial plateau 260 and may allow for full range of angular adjustment within compatible tibial revision-implant receivers 218.

The implant anchor 254b may also comprise one or more flanges, struts, or support structures 262 which extend from the stem 256 and join, meet, or connect with an underside of the tibial plateau 260, to provide support thereto.

Each tibial augment 216 preferably provides a half-plateau coverage and/or has a recess or shape complementary to receive one or more flanges 262 on one or both sides of the tibial implant 220.

In-use, in preparation for revision arthroplasty, in this case for a knee, a surgeon obtains at least one of the femoral component 12 and the tibial component 14 in the case of partial replacement, and preferably both in the case of rTKR.

In particular, the surgeon may obtain a femoral implant-replacement anchoring kit, comprising the revision-implant receiver 18 and the implant anchor 54b for the femoral component 12. The kit may further comprise the bearing surface 54a, and optionally one or more augments 16. Additionally or alternatively, the surgeon may obtain a tibial implant-replacement anchoring kit, comprising at least the revision-implant receiver 218 and the implant anchor 254b for the tibial component 14, and optionally the bearing surface 254a and/or one or more augments 216. If the kit comprises at least the revision-implant receivers 18,218 and the implant anchors 54b,254b for both the tibial and femoral components 12,14, then the kit may be considered to be a total implant-replacement anchoring kit, a joint replacement kit, a total joint replacement kit or a total implant-replacement kit.

In the present embodiment, the whole knee undergoes rTKR, such that both revision femoral and tibial components 12,14 are implanted, preferably simultaneously, but alternatively, it may be that only part of the joint is replaced, such that some of the following steps may be omitted. The method steps to implant the tibial component 14 are similar to those for implanting the femoral component 12. Detailed description of the common steps may be omitted for brevity.

The bearing surface 254a in the tibial component 14 may be engaged, preferably via insertion, with the tibial plateau 260, as best illustrated by arrow AA in FIG. 3, before or during surgery.

During surgery, the surgeon removes the pTKR and prepares the femur F and the tibia Ti to receive the rTKR. This involves the steps of preparing the bones to receive the first receiver elements 22,222 in accordance with the necessary alignment to the natural bone geometry. The alignment data may be obtained by any or any combination of techniques, methods, or tools. The techniques, methods or tools may include X-Rays, CT scans, MRI, XROMM, or any other suitable technique or combination thereof. The alignment data may additionally or alternatively be obtained intraoperatively. After obtaining alignment data, a trial reduction is undertaken before preparing the tibia and the femur to accommodate the second receiver elements 24,224. The final implant 220 is then prepared and inserted.

Obtaining Tibial Alignment Data

The tibia Ti is prepared for the first receiver element 222 using 'long stem' guided intramedullary (IM) hardware and a rasp. This involves cutting the tibia Ti to provide a suitable receiving cavity for the first receiver element 222. The intramedullary canal of the bone may need to be cut, rasped, and/or widened to provide the receiving cavity. Preferably, the receiving cavity is complementarily shaped to engage with the outer surface 230b of a sleeve body 228a of the tibial receiver 218, by having complementary stepped sections.

The orientation and the positions along the anterior-posterior and medial-lateral directions of the first receiver element 222 are driven by the native anatomy of the patient. Adjustment along the distal-proximal direction of the first receiver element 222 is possible at this stage. The tibial cut is positioned and oriented using extramedullary instruments. The relative flexion and varus/valgus angles between the tibial cut and the prepared receiving cavity for receiving the first receiver element 222 are recorded. The tibial cut and any required augment cuts are made. The rasp to create the receiving cavity for the first receiver element 222 is left in-situ and a tibial implant trial is attached to it using a linking component with provision for angular adjustments in any of the coronal plane C and the sagittal plane S, and for distal-proximal linear adjustment.

Obtaining Femoral Alignment Data

Figures 8, 9:
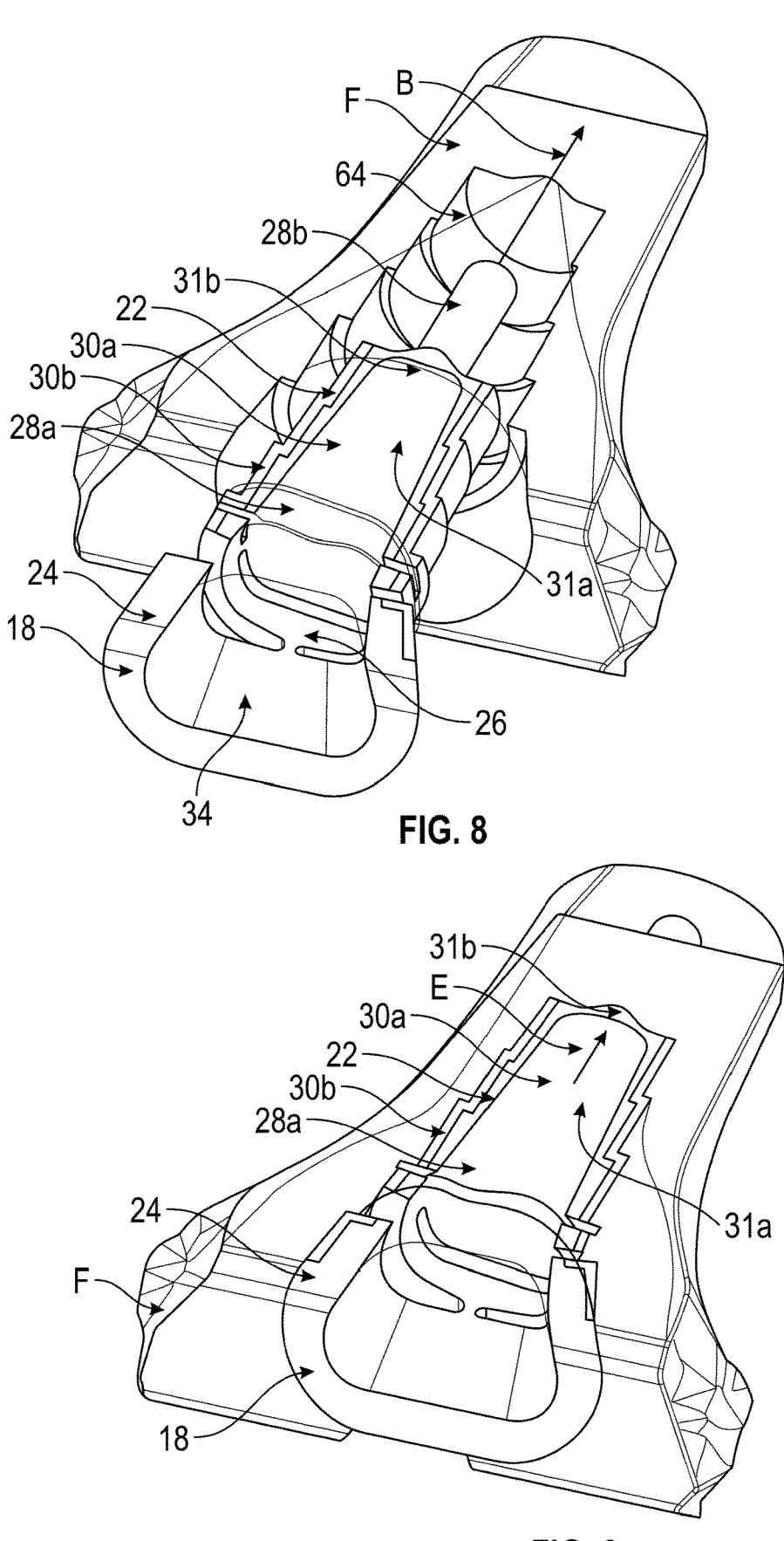
FIG. 8 shows a cutaway perspective representation of the insertion of the femoral revision-implant receiver of FIG. 2 in accordance with the first aspect of the invention, in a pre-bent condition, being inserted into the prepared femur.
FIG. 9 shows a cutaway perspective representation of the femoral revision-implant receiver of FIG. 8 being secured in the femur by press-fit impaction.

Similarly to the tibia Ti, the femur F is prepared for the first receiver element 22 using 'long stem' guided IM hardware and a rasp. This involves cutting the femur F to widen the intramedullary canal, as shown in FIG. 8, providing a receiving cavity 64 for the first receiver element 22. The intramedullary canal of the bone may need to be cut, rasped, and/or widened to provide the receiving cavity 64. Preferably, the receiving cavity 64 is complementarily shaped to engage with the outer surface 30b of a sleeve body 28a of the femoral receiver 18, by having complementary stepped sections.

The orientation and the positions along the anterior-posterior and medial-lateral directions of the first receiver element 22 are driven by the native anatomy of the patient. Adjustment along the distal-proximal direction of the first receiver element 22 is possible at this stage. The rasp used to form the receiving cavity 64 for the first receiver element 22 is left in-situ and a femoral implant trial is attached to it using a linking component with provision for angular adjustments in any of the coronal plane C and the sagittal plane S, and for distal-proximal linear adjustment.

Trial Reduction

A trial reduction checking any of, and preferably all of the range of motion (ROM), the balancing and assessment of the soft tissues is undertaken. Any angular and positional adjustments may be made to any of the following: the varus/valgus angles or angles in the coronal plane C of the tibial and/or femoral components 12,14; the tibial slope or angle of the tibial component 14 in the sagittal plane S; the positions of the tibial and/or femoral components 12,14 along the distal-proximal axis or direction; and the position of the femoral component 12 along the anterior-posterior axis through adjustment of flexion, in other words in the sagittal plane S. The relative coronal and sagittal angles between the trials and pre-prepared receiving cavities 64 for the tibial and femoral first receiver elements 22,222 are recorded.

Tibial and Femoral Preparation

The tibia Ti is prepared to accommodate the second receiver element 224 at the angles recorded in the previous steps, and most particularly at the adjustments to the position and the angles recorded in the trial reduction step.

Preparation of the tibia Ti involves using cutting or rasping instrumentation that references the pre-prepared receiving cavity for the first receiver element 222. In other words, the intramedullary canal is widened and shaped to also accommodate the second receiver element 224. The same steps are repeated on the femur F. Femoral cuts relative to the recorded angles and any required augment cuts are made to provide or enable any final angular adjustments. Additionally or alternatively, tibial cuts relative to the recorded angles and any required augment cuts are made to provide or enable any final angular adjustments. It may be however that no tibial and/or femoral cuts for final adjustments may be required.

Implant Preparation

The revision-implant receiver 18 of the femoral component 12 is bent, preferably prior to insertion into the bone. This is preferably done in-theatre and/or during surgery. However, the bending may be done outside of the theatre and/or prior to surgery. The reorientation may even be done during manufacture and/or in the factory. This involves re-orienting the second receiver element 24 relative to the first receiver element 22 via the hinge element 26, preferably using dedicated instrumentation. This is best illustrated in FIG. 5, in which the arrow A indicates rotation about the first pair 42a of linking portions 42. In FIG. 5, the dash-dotted outline indicates the starting position SP of the second receiver element 24 and the solid line outline indicates the end position EP of the second receiver element 24. The size of the first sub-gaps 48a has been altered as shown, as one side of the second receiver element 24 compresses or reduces the size of one first sub-gap 48a, whilst the opposing side of the second receiver element 24 increases the volume or size of the opposing first sub-gap 48a.

The femoral second receiver element 24 is bent relative to the first receiver element 22 to the angles recorded in trial reduction step. As there are preferably two, non-parallel hinge axes 52a,52b, the second receiver element 24 may be re-oriented around either or both hinge axes 52a,52b. In other words, the revision-implant receiver 18 may be bent in the coronal plane C and/or the sagittal plane S. Similar steps are undertaken for the tibial revision-implant receiver 218.

Implant Insertion

The femoral revision-implant receiver 18 is then inserted or introduced into the receiving cavity 64 in the prepared bone, as indicated by the arrow B in FIG. 8. Preferably no cement is inserted between the bone and the revision-implant receiver 18, but this alternative may be envisioned.

To ensure a secure engagement between the revision-implant receiver 18 and the surrounding bone, the revision-implant receiver 18 is impacted or hit further into the bone, as indicated by the arrow E in FIG. 9.

Figure 10:
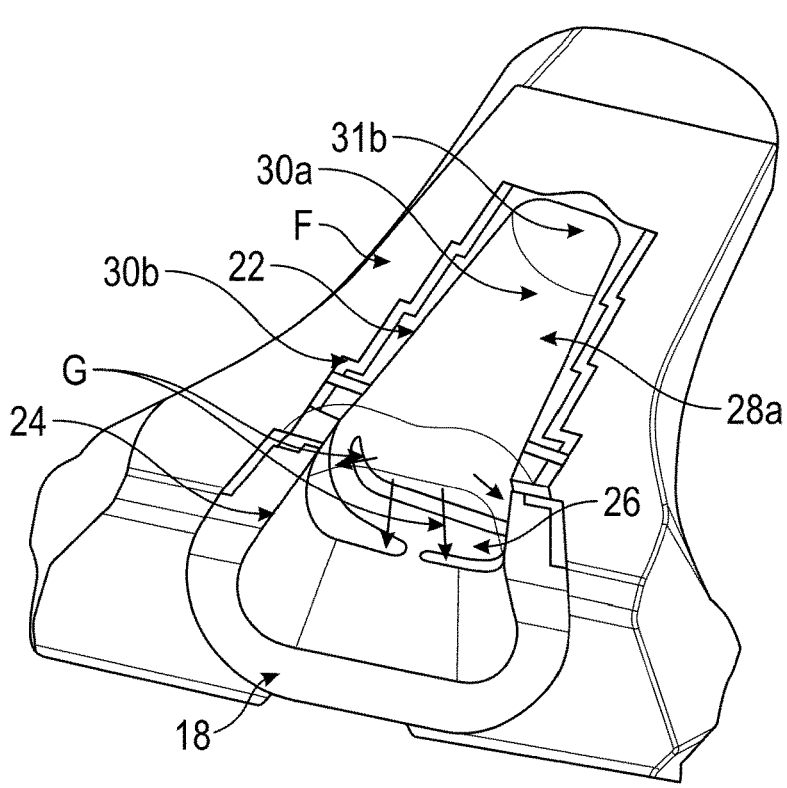
FIG. 10 shows a cutaway perspective representation of securing the angle between the first and second receiver elements of the femoral revision-implant receiver of FIG. 9 by inserting cement into hinge element gaps.

The angular orientation of the second receiver element 24 relative to the first receiver element 22 is set, secured, locked, or fixed before or, preferably, after insertion into the bone. Here, fixing the angular orientation involves inserting cement into one or more relevant gaps or cavities, but non-cement solutions, such as a mechanical insert or wedge may be envisioned instead of or in addition to cement. Cement insertion may be done in two or more steps. In the first step, cement is inserted into the first and/or second sub-gaps 48a,50a as indicated by arrows G in FIG. 10. Preferably, cement is also inserted into any other gaps or hollows other than the central cavity 34, such as the aperture 258 in the tibial component 14, but this is optional. At this stage, no cement is present in the central cavity 34. In the second step of cement insertion, bone cement is inserted into the central cavity 34. In the present embodiment, cement insertion or filling the cavities with cement is done in two or more steps. Inserting cement into the outer cavities or gaps, here the first and/or second sub-gaps 48a,50a first, reduces the risk of these cavities or gaps not being filled due to the bone cement in the central cavity 34 drying too quickly.

It could however be envisioned that cement insertion is done in one step. This may occur for instance if the size and/or position of the first and/or second sub-gaps is such that it is difficult or even impossible to access and/or accurately fill these sub-gaps in isolation. In this alternative, cement may be inserted into the central cavity and any gaps or sub-gaps simultaneously. The cement may be sufficiently fluid, deformable, or malleable to enter the gaps or sub-gaps prior to drying.

Figure 11:
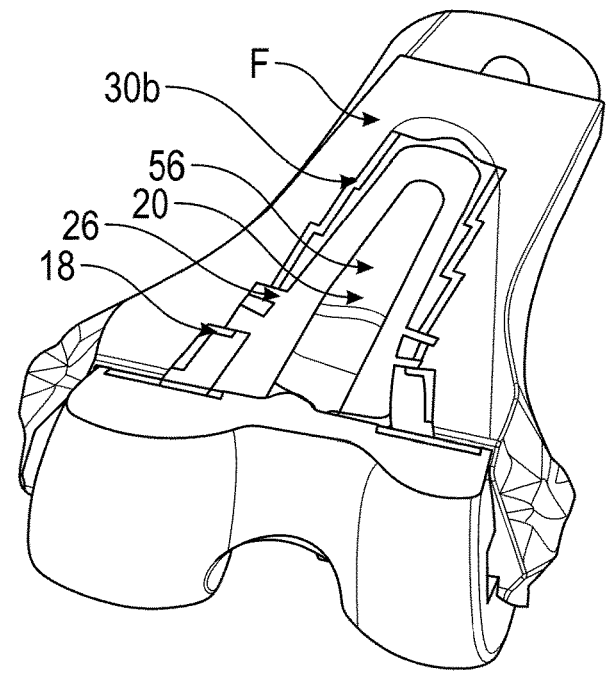
FIG. 11 shows a cutaway perspective representation of a femoral implant received and cemented in position within the femoral revision-implant receiver of FIG. 10.

As shown in FIG. 11, the stem 56 of the implant 20, which may also be pre-bent, is inserted into the central cavity 34, before, after, or simultaneously with bone cement inserted in the central cavity 34. The bearing surface 54a, if not integrally formed with the implant anchor 54b, may be connected to the implant anchor 54b secondarily. Augments 16, if required, are also appropriately positioned before the bearing surface 54a is made to contact or engage with the bone, directly or indirectly via the augments 16. The augments 16,216 may be used to adjust the position of the tibial implant 220 and/or the femoral implant 20 along any of the anterior-posterior direction, the distal-proximal direction, and medial-lateral direction.

The first receiver element 22,222 and the second receiver element 24,224 together provide deep metaphyseal fixation and augmentation. The mini-stem 28b of the first receiver element 22,222 stabilises, limits and/or reduces the damage to the natural bone. The central cavity 34 being filled with cement provides a cemented interface between the cone-like second receiver element 24,224 and the implant 20,220.

Once all the femoral and tibial components are implanted, the femoral bearing outer surface 54a is able to abut against, engage and articulate with the tibial bearing 254a. Final adjustments may be made before the wound is closed up.

Figures 12, 13, 14:
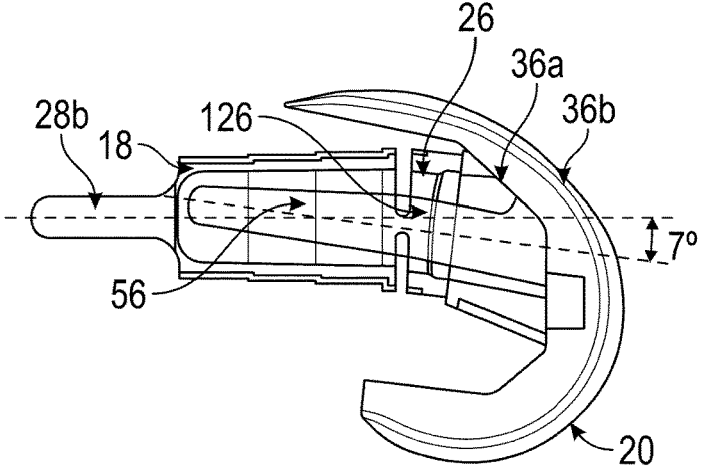
FIG. 12 shows a cutaway front view of the femoral component of the rTKR of FIG. 2, in which the bearing surface of the femoral implant is re-oriented in the coronal plane at a first coronal angle relative to the femur, the femur being omitted for clarity.
FIG. 13 shows a cutaway front view of the femoral component of the rTKR of FIG. 2, in which the bearing surface of the femoral implant is re-oriented in the coronal plane at a second coronal angle relative to the femur, the femur being omitted for clarity.
FIG. 14 shows a cutaway side view of the rTKR, in which the bearing surface of the femoral implant is re-oriented in the sagittal plane at a first sagittal angle relative to the femur, the femur being omitted for clarity.

FIGS. 12 and 13 show examples of second receiver elements 24 of femoral components 12 re-oriented in the coronal plane C at two different angles relative to the first receiver element 22. Specifically, the axis of the first receiver element 22 in both Figures deviates by the same angle relative to a same reference axis 66. The absolute value of the deviation angle is shown here to be 5° but any alternative absolute value of the angle may be envisioned, such as an angle within the range 0° to 15. The reference axis 66 may optionally be the mechanical axis of the femur.

Due to the hinge element 26, the axis of the second receiver element 24 of FIG. 12 is angled relative to the axis of the first receiver element 22 of FIG. 12, and relative to the axis of the second receiver element 24 of FIG. 13. As the increased contact area 40 of the truncation or chamfer 38 of the second receiver element 24 preferably at least partly abuts against the bearing surface 54a, more specifically against the inner face 36a thereof, re-orientation of the second receiver element 24 mechanically results in the re-orientation of the bearing surface 54a. Preferably, the inner face 36a abuts against the whole surface of the contact area 40. This may easily be achieved where the inner face 36a and the contact area 40 are complementarily-shaped, such as by being both planar, or by having complementary curved cross-sections. Thus a plane 68, indicated as a line in cross-section in FIGS. 12 and 13, tangential to the condyles of the implant 20 is at different angles relative to the same reference axis 66 in FIGS. 12 and 13. The coronal angle between the tangential plane 68 and the reference axis 66 may be contained within a, preferably continuous, range. The range may be 75° to 120°, more preferably is 85° to 115°, and most preferably 90° to 110°.

Whilst preferably, the inner face 36a abuts against the whole surface of the contact area 40, this may not necessarily be the case, due to the relative orientations of the inner face and the second receiver element. For instance, the inner face may not contact the whole surface of the contact area. The inner face may abut against only part of the contact area, or even only an edge of the contact area and/or receiver. The inner face and the contact area may abut along or substantially along a line. This may occur where the inner face and the contact area are non-complementarily-shaped.

By having at least one of the contact area 40 and the inner face 36a having curvature, some degree of internal and/or external rotational adjustment may be provided.

In FIG. 12, the plane 68 forms a 95° angle with the reference axis 66, whilst in FIG. 13, the corresponding angle is shown to be 86°.

Similarly, FIG. 14 shows an example of second receiver element 24 of the femoral component 12 re-oriented in the sagittal plane S relative to the first receiver element 22, instead of or in addition to the coronal plane C. In particular, FIG. 14 illustrates the sagittal angle between the longitudinal axes of the first receiver element 22 and the second receiver element 24. The absolute value of the sagittal angle may be between 0° and 50°, more preferably between 1° and 20°, and most preferably between 2° and 10°. The sagittal angle shown in FIG. 14 is 7°.

In FIG. 14, the stem 56 is shown to comprise a hinge element 26 but the hinge element may be omitted from the stem. As shown, the stem 56 extends linearly or substantially linearly and/or both the first stem portion 56a and the second stem portion 56b are aligned. In other words, the stem 56 may not necessarily be angled. The stem 56 may optionally contact or abut against the inner surface 30a of the sleeve body 28a. As the contact area therebetween may be small, any forces applied thereto by the stem 56 are localised to the small contact area, increasing the risk of structural failure of the receiver 18. Furthermore, the stem 56 may contact the receiver 18 at a second position. Cement may provide mechanical strength and/or spread out the forces. This may constrain or restrict the angular range. Additionally or alternatively, the interaction of the increased contact area 40 of the truncation 38 and the bearing surface 54a, more specifically the inner face 36a thereof, may result in the stem 56 being spaced-apart from at least the sides and/or the base of the inner surface 30a, as shown in FIG. 14.

The hinge element 126 of the implant 20, may allow the first stem portion 56a and the second stem portion 56b to be re-oriented relative to each other. The angular range may be increased and/or the contact area between the stem 56 and the inner surface 30a may be increased, resulting in greater stability and forces being distributed over a greater area. Preferably, the hinge elements 26,126 of the revision-implant receiver 18 and the implant 20 line up or coincide with each other, as shown in FIG. 14, but this may not necessarily be the case, and may depend on the relative dimensions of the receiver 18 and the stem 56, and/or how deep the stem 56 is inserted into the central cavity 34.

Thus, there is provided a method of improving the angular orientation of an implant in revision arthroplasty. The method includes the steps of providing a revision-implant receiver and a revision implant; and re-orienting or bending the second receiver element about the hinge element relative to the first receiver element and inserting a stem of the revision implant into the re-oriented or bent revision-implant receiver.

Figure 17:
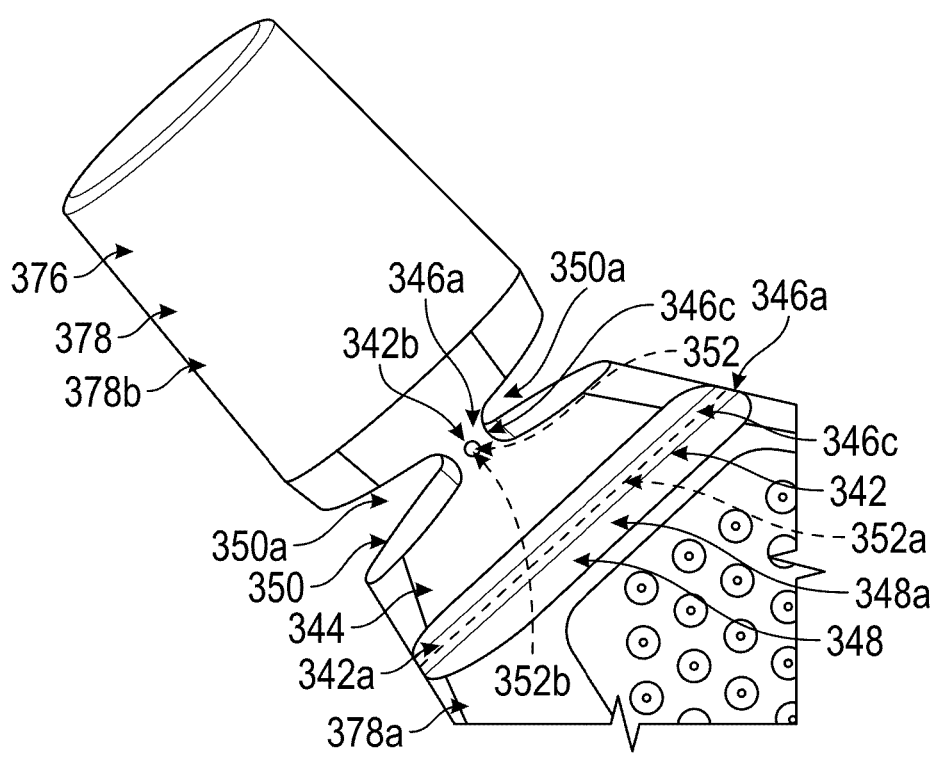
FIG. 17 shows an enlarged view of the square in FIG. 15.

Referring now to FIGS. 15 to 17, there is shown part of an implant 320 of a partial or total, preferably revision, joint replacement 310 for a hip. Partial hip arthroplasty involves replacing one of an acetabular component (not shown), and a femoral component 312, whilst total hip arthroplasty involves replacing both.

Features of the revision hip replacement 310 which are similar to the revision knee replacement 10 have similar references, with the prefix "3" added if no prefix was previously added, or replacing the previous prefix.

The femoral component 312 comprises a femoral revision-implant receiver, not shown, and the previously mentioned hip implant 320.

The femoral revision-implant receiver for a hip replacement 310 is similar to the femoral revision-implant receiver 18 for a knee replacement 10, having similar material properties, first receiver element, second receiver element, and hinge element. Detailed description of the common features is therefore omitted for brevity.

The hinge element of the hip revision-implant receiver is similar to the hinge element 26 of the knee revision-implant receiver 18, having at least one pair of linking portions. Preferably the hinge element comprises two pairs of linking portions, two hinges, and a spacer segment, although any of these features may be omitted. Detailed description of the common features is omitted yet again for brevity.

The hip implant 320 comprises a femoral ball, not shown, and an implant anchor 354b which comprises a hip stem 356. The hip stem 356 comprises a stem body 370 and a neck 372. The hip stem 356, and more particularly the neck 372 thereof, comprises a hinge element 326 as shown, although this feature may be omitted.

The stem body 370 is the portion of the stem 356 which is received within, surrounded, or enclosed by the femur. The stem body 370 comprises a body longitudinal axis 374, indicated as a dotted line in FIGS. 15 and 16. The stem 356 and the neck 372 may be integrally formed with each other, as shown, but connected or connectable, optionally by interference fit or tapers, may be alternatives.

The neck 372 extends from the stem body 370 towards the acetabulum and preferably at an angle relative to the body longitudinal axis 374. The neck 372 meets, joins, or connects with the femoral ball at the other end of the neck 372. If not integrally formed with the femoral ball, the neck 372 connects to the femoral ball via interference fit and/or complementary tapers or trunnions, of which only one taper 376, here the male taper, is shown in FIGS. 15 to 17.

The hinge element 326 of the hip implant 320 is similar to the hinge element 126 of the knee femoral implant 20, having at least one, and preferably two linking portions 342; a spacer segment 344; and at least one hinge axis 352. Each linking portion 342 has preferably two outward-facing surfaces 346a, two lateral surfaces 346c and a waisted portion 346d. For brevity therefore, detailed description of the common features is omitted.

Preferably, the hip stem 356 of part thereof has a non-circular cross-section, but circular may be envisioned. More specifically, at least one of: the neck 372 and the stem body 370, preferably the former, may be flattened such that it is non-circular in cross-section. The flattening may be in an anterior-posterior direction, as shown, although any other direction, such as medial-lateral and/or proximal-distal may be envisioned. Here, the stem body 370 or part thereof has a cross-section which may be a circle, but any other cross-section may be considered, such as curved, non-curved, part-curved, non-circular, an oval, ovoid, an ellipse, a polygon such as a rectangle or square, whether regular, irregular, truncated or chamfered, a rectangle or square with at least one rounded corner and/or edge, a circle in which the two halves are spaced-apart from each other, or any other desirable shape in cross-section. The outward-facing surfaces 346a of the linking portions 342 are preferably curved in lateral and/or longitudinal cross-section, and more preferably are convex, although non-curved, or even planar or substantially planar may be envisioned.

The hinge element 326 defines or divides the neck 372 into two neck portions 378, the first of which engages with the stem body 370, and the second of which comprises the taper 376. The hinge element 326 is preferably spaced-apart from the taper 376. This is because the engagement of the femoral ball and the neck may prevent or inhibit any bending or re-orientation about the hinge element if the hinge element is at or too close to the tapers. Alternatively, engagement of the femoral ball with the neck may be prevented or inhibited if the neck is hinged and bent at the tapers. In other words, the neck's taper may no longer be complementarily formed with the femoral ball's taper. For similar reasons, the hinge element 326 is preferably also spaced-apart from the stem body 370.

The first neck portion 378a is connected with the spacer segment 344 by a first of the linking portions 342, referred to as the first linking portion 342a for clarity. As the neck is part of the stem, the first neck portion 378a may be referred to as a first stem portion. The first linking portion 342a defines the first said hinge axis 352, referred to as a first hinge axis 352a for clarity. The first hinge axis 352 preferably extends in a plane which is shown to be the coronal plane or a plane parallel thereto, although alternatives may include the sagittal plane or any other plane. The first linking portion 342a defines two first sub-gaps 348a which together form a first gap 348. The first neck portion 378a further comprises a first neck longitudinal axis 380a, indicated as a dashed line in FIGS. 15 and 16. The first hinge axis 352a is preferably perpendicular to the first neck longitudinal axis 380a as shown.

Similarly, the second neck portion 378b is connected with the spacer segment 344 by the second of the linking portions 342, referred to as the second linking portion 342b for clarity. As the neck is part of the stem, the second neck portion 378b may be referred to as a second stem portion. The second linking portion 342b defines the second said hinge axis, referred to as a second hinge axis 352b for clarity. The second hinge axis 352b is preferably non-parallel to the first hinge axis 352a. More preferably, the second hinge axis 352b extends perpendicularly to the first hinge axis 352a. As such, the second hinge axis 352b preferably extends in or parallel to the sagittal plane S although any other plane, including the coronal plane C may be envisioned. The second linking portion 342b also defines two second sub-gaps 350a which together form a second gap 350. The second neck portion 378b also comprises a second neck longitudinal axis 380b, indicated as dashed lines in FIGS. 15 and 16. The second hinge axis 352b is preferably perpendicular to the second neck longitudinal axis 380b.

When the first and second neck portions 378a,378b are aligned relative to each other, their neck longitudinal axes 380a,380b are co-linear and/or parallel with each other. However, when the second neck portion 378b is re-oriented relative to the first neck portion 378*a*, the neck longitudinal axes 380*a*,380*b* are non-colinear and/or non-parallel. At least one of the neck longitudinal axes 380*a*,380*b* is preferably angularly offset in the coronal plane C relative to the body longitudinal axis 374.

The uses of the preferably hinged, revision-implant receiver and/or the preferably hinged, hip implant 320 are similar to the uses of the previous embodiments. Detailed description of the common steps is therefore omitted for brevity once again. As the hinge element 326 of the femoral implant 320 is preferably in-use outside of the femur F, the neck 372 and/or femoral ball may be re-oriented relative to the stem body 370 before or after insertion of the stem body 370 into the bone and/or revision-implant receiver. The femoral ball may be connected at any point before or after insertion of the stem body 370 into the femur F and/or before or after the re-orientation of the neck taper 376.

Figure 18:
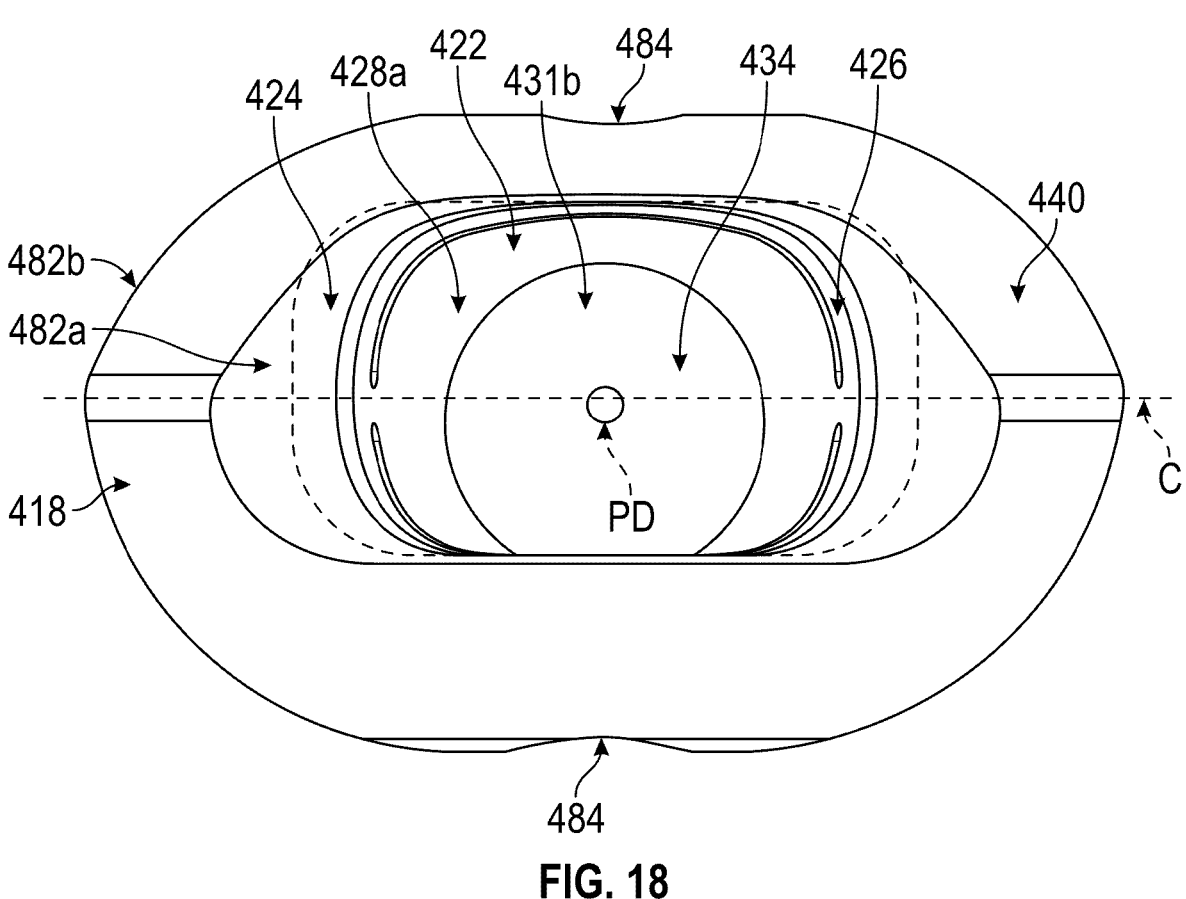
FIG. 18 shows a plan view of a fourth embodiment of a revision-implant receiver, in accordance with the first aspect of the invention.

Referring now to FIG. 18, there is shown a fourth embodiment of a revision-implant receiver 418 which is similar to the first embodiment of the revision-implant receiver 18, having similar first receiver element 422, second receiver element 424, sleeve body 428*a*, hinge element 426, mini-stem, truncation and increased contact area 440, although the last four features may be omitted. For brevity, detailed description of the common features is omitted. Features of the fourth embodiment of the revision-implant receiver 418 which are similar to the features of the first embodiment have similar reference numerals with the prefix "4" added.

The fourth embodiment of the revision-implant receiver 418 may be used as part of a tibial component, a femoral component, whether for the knee or the hip, or in arthroplasty of any other desirable joint, whether primary or revision. In the fourth embodiment, the central cavity 434 may change in lateral cross-section along the proximal-distal axis PD, shown as a dot in FIG. 18. The receiver 418 and/or central cavity 434 may be circular or substantially circular, or elliptical in lateral cross-section at or adjacent to the base end 431*b*. Preferably, as shown, the cross-section of the central cavity 434 may be partly truncated or chamfered. The truncation may occur in a plane parallel to the coronal plane C, indicated as a dashed line. The lateral cross-section transitions in a direction of the first receiver element 422 to the second receiver element 424 preferably continuously or substantially continuously. The lateral cross-section of the receiver 418 and/or the central cavity 434 transitions from a truncated circle into or substantially into two portions of an ellipse or circle which are spaced-apart from each other, preferably along the medial-lateral axis, not shown. This lateral cross-section may alternatively be described as a rectangular or substantially rectangular cross-section, which may or may not have one or more rounded corners and/or one or more curved edges. As shown in FIG. 18, the central cavity 434 and/or the second receiver element 424 or at least an inner surface 482*a* thereof has the above-described lateral cross-section, indicated as a dashed outline. An outer surface 482*b* of the second receiver element 424 has a different cross-section to the inner surface 482*a*, but the same cross-section may be envisioned. Here, the outer surface 482*b* in lateral cross-section may be or be substantially an ellipse or a flattened ellipse. The lateral cross-section may optionally have at least one indent, groove, or concave portion 484. It may alternatively be envisioned that instead of an indent, one or a plurality of protrusions and/or a localised thickening of the revision-implant receiver may be provided. Said concave portion 484 may optionally be partway along a major dimension or diameter of the cross-section, and/or may be provided on one or on both opposing sides of the ellipse. The or each concave portion 484 describes a waist. As shown, the lateral cross-section of the outer surface 482*b* loosely describes a figure of eight shape, an hourglass shape, a peanut shape, or an elongate element having two lobes. The cross-sectional shapes of the inner and outer surfaces may even be reversed such that the inner surface may comprise the concave portions instead. The uses of the fourth embodiment are similar to those of the any of the previous embodiments. Detailed description of the common features is omitted, once again, for brevity.

Figure 19:
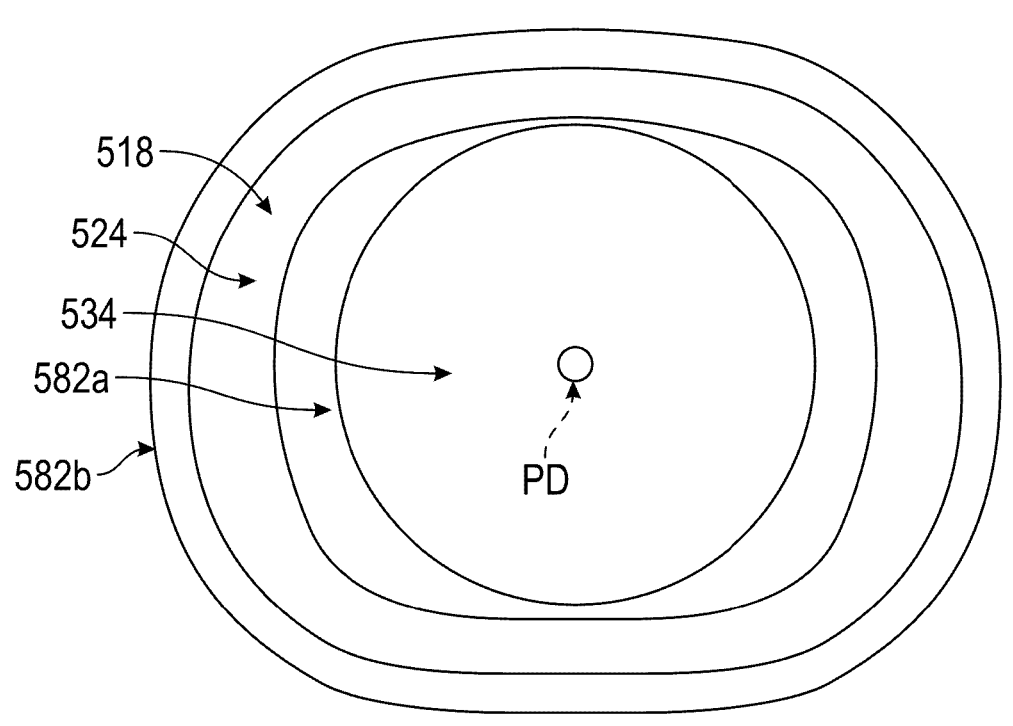
FIG. 19 shows a plan view of a fifth embodiment of a revision-implant receiver, in accordance with the first aspect of the invention, with a hinge element and a first receiver element omitted for clarity.

Referring now to FIG. 19, there is shown a fifth embodiment of a revision-implant receiver 518, with the hinge element and the first receiver element omitted for clarity. The revision-implant receiver 518 is similar to the first embodiment of the revision-implant receiver 18, having similar first receiver element, second receiver element 524, sleeve body, hinge element, mini-stem, although the last two features may be omitted. For brevity, detailed description of the common features is omitted. Features of the fifth embodiment of the revision-implant receiver 518 which are similar to the features of the first embodiment have similar reference numerals with the prefix "5" added.

The fifth embodiment of the revision-implant receiver 518 may be used as part of a tibial component, a femoral component, whether for the knee or the hip, or in arthroplasty of any other desirable joint, whether primary or revision. Preferably, the second receiver element 524 is not truncated such that the truncation or chamfer is omitted, however, this feature may easily be envisioned. In the fifth embodiment, the central cavity 534 may change in lateral cross-section along the proximal-distal axis PD. The receiver 518 or at least the inner surface 582*a* and/or central cavity 534 may be circular or substantially circular, or elliptical in lateral cross-section, at or adjacent the hinge element, not shown. The lateral cross-section transitions, preferably continuously or substantially continuously in a direction of the first receiver element to the second receiver element 524. The lateral cross-section of the second receiver element 524, or at least one of the inner surface 582*a* and the outer surface 582*b* thereof transitions into a rectangular or substantially rectangular cross-section, which may or may not have one or more rounded corners and/or one or more curved edges. Additionally or alternatively, the cross-section of one, or both the outer surface 582*b* and the inner surface 582*a* may transition into or substantially into two portions of an ellipse or circle spaced-apart from each other, preferably along the medial-lateral axis. The uses of the fifth embodiment, similar to those of any previous embodiment, are omitted for brevity.

In other words, there is provided a method of improving the angular orientation of an implant in revision arthroplasty. The method has the steps of providing a revision implant and a revision-implant receiver, either or each of the revision implant and the revision-implant receiver having two hingeably connected portions. The relative angle between the two hingeably connected portions of one or both the revision implant and the revision-implant receiver is adjusted to improve the angular orientation of the revised or revision implant in one or more planes. Said planes may be the coronal plane C and/or the sagittal plane S, but alternative or additional planes may be considered.

Although the above embodiments disclose knee joint and/or hip joint replacements or replacements of an existing tibial and/or femoral implant for the knee and hip, the joint replacement may be adapted for a shoulder, an elbow, an ankle, a finger, a toe, or any other desirable joint.

In the above embodiments, the revision joint replacements are total replacements, such that all components are revised. It could alternatively be envisioned that the revision joint replacement may be a revision partial joint replacement. In this case, it may be that only part of the primary implant may be revised or replaced. For example, only a revision knee or hip femoral component may be implanted, whilst the complementary part of the primary joint replacement is maintained, for example a primary tibial component or the primary acetabulum in the above examples. Thus, the revision femoral component is articulable with the primary component, or vice versa. The revision partial joint replacement may even be articulable with the original bone, where the primary implant being revised only replaced part of a joint. Similarly, it may be envisioned that the primary implant may be suitable for use with a revision-implant receiver. It may even be feasible that a revision implant anchor may be usable with a primary bearing surface.

Whilst the implant receiver and the implant, whether a primary or revision implant, are separable from each in any of the above embodiments, it may alternatively be envisioned that implant and the implant receiver may be non-separable. The implant and the implant receiver may be connectable or connected to each other, such as by a mechanical connector, or may even be integrally formed as a one piece. The implant receiver may comprise a mechanical connection means or connector, such as an extension, protrusion or plate, and the bearing surface may comprise a complementary mechanical connection means or connector, such as an extension, protrusion, or plate. The respective connection means may engage with other directly and/or require a fastening element or fastener, such as a bolt. For example, the implant and the receiver may comprise each a plate having at least one bolt-hole such that the implant and receiver may be boltable together.

It may even be envisioned that in addition to or instead of a stem, the implant may comprise the or a said second receiver element or portion, and/or a cone or sleeve which may be engageable or receivable within the revision-implant receiver. If the implant comprises both a stem and a second receiver element, the second receiver element or cone or sleeve may be connectable, connected or integrally formed with the stem. Alternatively, the second receiver element, cone or sleeve may not be connectable, connected or integrally formed with the stem. Instead, the second receiver element, cone or sleeve may be engageable or engaged with the bearing surface of the implant. Such an implant may optionally still comprise at least one hinge element or hinge. The stem may comprise the or a said hinge element. Alternatively or additionally, a hinge element may be provided between the bearing surface and the second receiver element.

Whilst all the above embodiments relate to revision arthroplasty, any primary or non-revision components may incorporate features of the revision components. For instance, it may be conceived that a primary implant receiver, and/or primary implant may comprise a hinge element as described above.

Where the remaining bone is of sufficient quality, the, preferably hinged, implant or revision implant may be engaged directly with the bone such that the revision-implant receiver of either or both the femoral and tibial components may be omitted entirely, during primary or revision surgery. In other words, the above hip or knee femoral implant and/or tibial implant may be used without compatible femoral and/or tibial revision-implant receivers if adequate cemented fixation can be achieved, preferably at the epiphyseal mating surfaces and/or along the length of the stem.

In any of the above embodiments, any of: the implant or part thereof, the first receiver or part thereof, and the second receiver or part thereof, may further be coated with plasma-sprayed and/or electrochemically deposited materials such Hydroxyapatite and/or Titanium. These deposited materials may increase the friction fit to the bone and/or encourage bone growth, therein, thereagainst or therearound, between the bone and implant receiver and/or implant. The coating may also have antibacterial properties by inclusions of silver, copper, or other known substances. Similarly, in any of the above embodiments, any of: the implant or part thereof, the first receiver, and second receiver may be manufactured by 3D printing or Additive Manufacturing methods (AM) which involves building the parts from typically digital 3D files rather than removing material from bar or forgings using conventional cutting machinery. Such AM methods allow increased flexibility to incorporate complex shapes/forms and this allow a porous type bone enhancing surface into the necessary bone contact areas of any of: the implant or part thereof, the first receiver, the second receiver, and any combination thereof.

Whilst in all the above embodiments, the hinge element only has one spacer segment, a plurality of spacer segments may be a desirable option. Two spacer segments may be connected to each other by one or more linking portions and/or by non-bendable connections. Multiple spacer segments or elements provide a greater range of angular adjustments and/or angular adjustments in a greater number of planes. The revision-implant receiver and/or the implant may even be formed in a bent configuration, rather than being formed secondarily.

Whilst in the present embodiments, the lateral surfaces are square or rectangular in side view and concave preferably along their entire length or width when viewed at a right angle, alternative cross-sections may be considered. For instance, one or both lateral surfaces may be non-concave and/or non-square or non-rectangular. More specifically, one or both lateral surfaces or part thereof may be curved, non-curved, planar, linear, polygonal whether regular, irregular, truncated or chamfered in longitudinal and/or lateral cross-section. Alternatively or additionally, each lateral surface may have an indented section along their width or longitudinal extent. Said indent or indented portion may be considered to be or be substantially in longitudinal and/or lateral cross-section curved, non-curved, part-curved, concave, convex, linear, polygonal such as triangular, whether regular, irregular, truncated, chamfered, tapering inwards to the narrowest point, a trapezium, a trapezoid, a square, a rectangle, a pentagon, hexagon, octagon, or any other desirable cross-sectional shape which may enable bending. Whilst a preferred shape may have been specified for any of the above features, any alternative shape in any of longitudinal, lateral and/or transverse cross-section may be envisioned. The shape may be curved, non-curved, part-curved, concave, convex, a circle, an ellipse, linear, polygonal, whether regular, irregular, truncated, chamfered, tapering inwards to the narrowest point, a trapezium, a trapezoid, a square, a rectangle, a pentagon, hexagon, octagon, or any abstract shape.

Although the stem is integrally formed with the bearing surface in the knee femoral embodiment, is integrally formed with the tibial tray in the tibial embodiment, and is connectable to the femoral ball via tapers in the hip embodiment, the stem and/or implant anchor in any of the embodiments may be integrally formed with the bearing surface and/or tibial tray, or may be connected or connectable thereto. The connection may be mechanical. The implant may even comprise at least one connector means or connector. Each connector may have first and second connector portions. The first and second connector portions may be complementarily engageable with each other. The implant anchor may be connected or connectable to the bearing surface and/or tibial tray by comprising the first connector portion and the bearing surface may comprise the second connector portion. The stem and/or implant anchor may be connected to the bearing surface and/or tibial tray by being at least one of: engageable via interference fit, boltable, screwable, connectable via an adhesive, cementable to the bearing surface and/or tray, abuttable and constrainable by the shape and/or form of interlocking features, and any other suitable means of connection.

In all the above embodiments, the stem of the implant, the inner surface and/or outer surface of the first receiver element or portion, the inner surface and/or outer surface of the second receiver element each stepped portion of the first receiver element, and the hinge element are or are substantially smooth. In an alternative embodiment, any or any combination of the above features may be non-smooth. More specifically, any of the above-mentioned features may have one or more grip-enhancing portions or elements. A grip-enhancing portion may include any of: a protrusion, a projection, a fin, a groove, a recess, a dimple, a ring, a notch, a concave portion, a convex portion, or any other suitable grip-enhancing portion. This improves the engagement between two elements, such as between the implant-receiver and the bone, or the bone cement and the implant. In particular, the stem of the implant may have one or more circular grooves. The circular grooves may be concentric about a central axis of the stem, and/or spaced-apart along a longitudinal extent of the stem or part thereof. These circular grooves improve the engagement of the implant with the bone cement, thereby preventing or inhibiting removal of the implant from the cement.

If any hinged component of the revision implant replacement comprises ceramics, each linking portion may need to comprise a non-ceramics material to enable bending at the waisted portion. Such a linking portion may not necessarily be integrally formed with the spacer segment and/or the receiver element or stem portion.

In all the above embodiments, the receiver requires at least one pair of linking portions to define a hinge axis. It could be envisioned however, that one linking portion may be sufficient to define the hinge axis of a receiver. Said linking portion may need to be sufficiently rigid to withstand, prevent or inhibit bending in directions other than the desired direction. For instance, such as linking portion may need to be able to prevent or inhibit the size of the gap between the first and second receiver elements from being altered, e.g. by the second receiver element being moved towards or away from the first receiver element on the opposite side of the central cavity.

Preferably, the hinge axes are spaced-apart from each other longitudinally. This avoids one linking portion, which is bendable along one axis, but rigid in all other directions, interfering with the bending ability of a second hinge axis. In an alternative embodiment, the hinge axes may be co-planar and non-parallel. In such an embodiment, the spacer segment may be omitted entirely. In this alternative, the at least two linking portions or pairs of linking portions, each defining a hinge axis may need to be deformable in multiple directions and/or compressible. An example of such as linking portions may be a plurality of springs or spring elements spaced around the gap between any of combination of: the first receiver element, the second receiver element, and the spacer segment. The linking portions may be equidistant from each other. When the second receiver element is bent along one hinge axis, preferably formed by two springs, the springs of the other or other hinge axes are compressed or extended, depending on the direction of bending.

The spacer segment may be omitted entirely such that the receiver and/or implant may have only one linking portion or pair of linking portions, connecting the first and second receiver elements directly. The linking portion is a strip or pillar in the present embodiment, having a waisted portion to enable bending. The linking portions may not necessarily be live hinges. A said linking portion may be insertable, connectable, connected to any of the spacer segment, the first receiver element or stem portion, the second receiver element or stem portion. Any of the spacer segment, the first receiver element, the first stem portion, the second receiver element, and the second stem portion may further have at least one first engagement portion. The linking portion may have at least one second engagement portion, complementarily engageable with the or each first engagement portion. The engagement portions may be complementary male and female features. By way of example only, the spacer segment and/or the first receiver element or first stem portion may comprise a female portion, groove or recess and the linking portion may have a complementarily-shaped male portion, insertable into the or each female portion, or vice-versa. Similarly, the spacer segment and/or the second receiver element or second stem portion may comprise a female portion and the linking portion may comprise a complementarily-shaped male portion, or vice-versa. A linking portion may be integrally formed at one end and connectable at the other. Further alternatives may be envisioned, for instance, a ball-bearing or ball-bearing system. The ball bearing may be centrally positioned relative to a stem. In an implant receiver, a pair of diametrically opposed ball bearing may be provided. Such a system would provide angular adjustment in a greater range of planes. Additionally or alternatively a lockable hinge system may be used.

It is therefore possible to provide a partial or full prosthetic joint for, preferably revision, arthroplasty. The same range of positioning as in existing solutions is provided. However, the prosthetic joint additionally provides angular orientation adjustment of the implant bearing surface or surfaces, unlike existing solutions, which provide only a fixed angular relationship between the intramedullary canal of the bone and the stem received within. The angular orientation may furthermore be adjusted in a plurality of planes, providing an improved implant fit and/or improved knee balancing. The ability to adjust the orientation of one or more components of the joint enables a reduction in the inventory stock that must be stored, saving space and costs, as well as reducing the complexity and duration of the surgery. The prosthetic joint also enables different surgical alignment approaches to be used. It is therefore also possible to provide an implant anchor which may provide modularity by enabling different bearing surfaces to be attachable thereto. The adjustability of the stem reduces the number of different stems that must be stocked. It is therefore also possible to provide a kit to provide choice if partial arthroplasty is required. It is therefore also possible to provide methods for adjusting the angular orientation and the positioning of an implant, to improve the fit thereof, and reduce the likelihood of a further revision being required. The words 'comprises/comprising' and the words 'having/including' when used herein with reference to the present invention are used to specify the presence of stated features, integers, steps or components, but do not preclude the presence or addition of one or more other features, integers, steps, components or groups thereof. It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination. The embodiments described above are provided by way of examples only, and various other modifications will be apparent to persons skilled in the field without departing from the scope of the invention as defined herein.

The invention claimed is:

1. A revision-implant receiver for supporting an implant of a revision joint replacement, the revision-implant receiver-comprising a first receiver element and a second receiver element-which is engaged via a hinge element with the first receiver element;

wherein the first receiver element and the second receiver element define together a central cavity for receiving a stem of the implant therein, and the hinge element comprises a first pair of bendable linking portions between the first receiver element and the second receiver element, each bendable linking portion of the first pair being positioned on either side of the central cavity to define a first hinge axis, wherein the hinge element comprises a second pair of bendable linking portions between the first receiver element and the second receiver element, each bendable linking portion of the second pair being positioned on either side of the central cavity and defining a second hinge axis;

wherein the hinge element comprises a spacer segment which is positioned between the first receiver element and the second receiver element, said spacer segment being hingeably engaged with the first receiver element by the first pair of bendable linking portions, and with the second receiver element by the second pair of bendable linking portions such that the second hinge axis is spaced-apart from the first hinge axis.

2. The revision-implant receiver of claim 1, wherein the first receiver element and/or second receiver element comprises a recessed portion and a one of said bendable linking portions extends from the recessed portion, the recessed portion thereby elongating the linking portion.

3. The revision-implant receiver of claim 2, wherein an outer surface of the linking portion and/or the said recessed portion is recessed radially inwardly relative to an outer surface of one or both the first receiver element and second receiver element, and/or wherein an inner surface of the linking portion and/or the recessed portion is recessed radially inwardly relative to an inner surface of one or both the first receiver element and second receiver element.

4. The revision-implant receiver of claim 2, wherein the linking portion and the recessed portion meet at a junction, the linking portion transitioning continuously into the recessed portion at the junction.

5. The revision-implant receiver of claim 1, wherein one of the first hinge axis and the second hinge axis extends in one of: an anterior-posterior direction, and a medial-lateral direction.

6. The revision-implant receiver of claim 1, wherein the second hinge axis is non-parallel with the first hinge axis.

7. The revision-implant receiver of claim 6, wherein the second hinge axis is perpendicular to the first hinge axis.

8. The revision-implant receiver of claim 1, wherein the first pair of bendable linking portions is integrally formed as a one piece with the spacer segment and the first receiver element; and/or the second pair of bendable linking portions is integrally formed as a one piece with the spacer segment and the second receiver element.

9. The revision-implant receiver of claim 1, wherein the first receiver element or an inner surface thereof is or is substantially a truncated cone.

10. The revision-implant receiver of claim 1, wherein the second receiver element is a trapezium in cross-section in the coronal plane, and one of: a circle, an ellipse, an oval, and a rectangle with one or more rounded edges and/or one or more rounded corners in cross-section in a transverse plane.

11. A method of improving an angular orientation of an implant in revision arthroplasty, the method having the steps of:

a) providing a revision implant and a revision-implant receiver, said revision-implant receiver comprising:

a first receiver element and a second receiver element which is engaged via a hinge element with the first receiver element;

wherein the first receiver element and the second receiver element define together a central cavity for receiving a stem of the implant therein, and the hinge element comprises a first pair of bendable linking portions between the first receiver element and the second receiver element, each bendable linking portion of the first pair being positioned on either side of the central cavity to define a first hinge axis, wherein the hinge element comprises a second pair of bendable linking portions between the first receiver element and the second receiver element, each bendable linking portion of the second pair being positioned on either side of the central cavity and defining a second hinge axis;

wherein the hinge element comprises a spacer segment which is positioned between the first receiver element and the second receiver element, said spacer segment being hingeably engaged with the first receiver element by the first pair of bendable linking portions, and with the second receiver element by the second pair of bendable linking portions such that the second hinge axis is spaced-apart from the first hinge axis; and adjusting a relative angle between the two hingeably connected portions of the revision-implant receiver to improve the angular orientation of the revision implant in a coronal plane and/or in a sagittal plane.

* * * * *